United States Patent [19]

Old et al.

[11] Patent Number: 5,712,369
[45] Date of Patent: Jan. 27, 1998

[54] ISOLATED PROTEIN WHICH BINDS TO A33 ANTIBODY, AND PEPTIDES CORRESPONDING TO PORTIONS OF THE PROTEIN

[75] Inventors: Lloyd J. Old; Sydney Welt; Gerd Ritter, all of New York, N.Y.; Richard J. Simpson, Victoria, Australia; Edouard Nice, Victoria, Australia; R. L. Moritz, Victoria, Australia; B. Catimel, Victoria, Australia; Hong Ji, Victoria, Australia; Anthony W. Burgess, Victoria, Australia; Joan K. Heath, Victoria, Australia; Sara J. White, Victoria, Australia; Cameron Johnstone, Victoria, Australia

[73] Assignee: Ludwig Institute for Cancer Research, New York, N.Y.

[21] Appl. No.: 597,495

[22] Filed: Feb. 2, 1996

Related U.S. Application Data

[63] Continuation-in-part of Ser. No. 511,876, Aug. 4, 1995, abandoned.

[51] Int. Cl.[6] .................. C07K 14/00; A61K 39/00; A61K 39/38; A61K 38/00
[52] U.S. Cl. ................ 530/350; 424/184.1; 424/185.1; 530/300; 530/324; 530/326; 530/327; 530/328
[58] Field of Search ................ 530/350, 300, 530/324, 326, 327, 328; 424/184.1, 185.1

[56] References Cited

PUBLICATIONS

Welt et al. (1994) J. Clin. Oncol. 12:1561–71.
King et al. (1995) Br. J. Cancer 72:1364–72.
Daghighian et al. (1996) J. Nucl. Med. 37:1052–57.

*Primary Examiner*—W. Gary Jones
*Assistant Examiner*—Amy Atzel
*Attorney, Agent, or Firm*—Felfe & Lynch

[57] ABSTRACT

This invention relates to isolated protein and to peptides which are found on the surface of colon cells and colon cancer cells, as well as to nucleic acid molecules encoding said protein and peptides. The protein and peptides bind to tumor-associated antibodies, such as mAb A33. The monomeric protein has a molecular weight of about 43 kD as determined by SDS gel electrophoresis under non-reducing conditions. In addition, this invention relates to the use of said nucleic acid molecules, protein, in monomeric or multimeric form, and to antibodies to said peptides in diagnostic, screening and therapeutic methods. This invention further relates to antibodies specific for said protein, in monomeric or multimeric form, and to antibodies to said peptides.

7 Claims, 20 Drawing Sheets

FIG. 12

| Sample | Sequence | Reference |
|---|---|---|
| 1. N-terminal | ISVETPQDVLRASQGKSVTLPCTYHTSTSSDREGLIQWDKL (SEQ ID NO: 4) | HP-414 |
| 2. D-1 | DVLRASQGKSVTLPCTYHTSTSSREGLIQW (SEQ ID NO: 5) | HP-463 |
| 3. D-2 | DKLLLTHTERVVIWPFSNKNYIHGELYKNRVSISNNAEQ (SEQ ID NO: 6) | HP-462 |
| 4. D-3 | ELYKNRVSISNNAEQ (SEQ ID NO: 7) | HP-461 |
| 5. D-4 | DXGTYECSVSLM (SEQ ID NO: 8) | HP-466 |
| 6. Pc-1 | IQLTCQSKEGSPTPQY (SEQ ID NO: 9) | HP-467 |
| 7. Pc-2 | LVLVPPSKPECGIEGEETIIGN (SEQ ID NO: 10) | HP-468 |
| 8. P-1 | ILNQGQPLAQPASGEPV (SEQ ID NO: 11) | HP-464 |
| 9. T-1 | EAYEEPPEQLR (SEQ ID NO: 2) | HP-379 |
| 10. T-2 | VVIWPFSNK (SEQ ID NO: 3) | HP-385 |

Note: 1 Peptide nomenclature: D, Asp-N-endoproteinase, t, trypsin, P, pepsin, Pc, peptides recovered from core material following therolysin/pepsin/Asp-N treatment of A33 antigen.
2 Pepetide D-4; residue X is considered an N-gylcosylated asparagine (motif: NXT); peptide mapping reveals that the cysteines in D-4 and the N-terminal sequence are connected via a disulphide bond.
3 Peptide D-1 is contained within the N-terminal sequence; peptides D-3 and T-2 are contained within peptide D-2.
4 The presence of at least one glycosylated site would indicate that the molecular weight of th A33 antigen is much lower than that observed on SDS-PAGE.

FIG. 16A

```
          10        20        30        40
GGGACTCCAGTTGGGCCAGGCCAGAAGCTGCTGTAGCTTT   40
AACCAGACAGCTCAGACCTCTATGGAGGCTGCCAGTGACA   80
GGTTAGGTTTAGGGCAGAGAAGAAGCAAGACCATGGTGGG  120
GAAGATGTGGCCTGTGTTGTGGACACTCTGTGCAGTCAGG  160
GTGACCGTCGATGCCATCTCTGTGGAAACTCCGCAGGACG  200
         210       220       230       240
TTCTTCGGGCTTCGCAGGGAAaGAGTGTCACCCTGCCCTG  240
CACCTACCACACTTCCACCTCCAGTCGAGAGGGACTTATT  280
CAATGGGATAAGCTCCTCCTCACTCATACGGAAAGGGTGG  320
TCATCTGGCCGTTTTCAAACAAAAACTACATCCATGGTGA  360
GCTTTATAAGAATCGCGTCAGCATATCCAACAATGCTGAG  400
         410       420       430       440
CAGTCCGATGCCTCCATCACCATTGATCAGCTGACCATGG  440
CTGACAACGGCACCTACGAGTGTTCTGTCTCGCTGATGTC  480
AGACCTGGAGGGCAACACCAAGTCACGTGTCCGCCTGTTG  520
GTCCTCGTGCCACCCTCCAAACCAGAATGCGGCATCGAGG  560
GAGAGACCATAATTGGGAACAACATCCAGCTGACCTGCCA  600
         610       620       630       640
ATCAAAGGAGGGCTCACCAACCCCTCAGTACAGCTGGAAG  640
AGGTACAACATCCTGAATCAGGAGCAGCCCCTGGCCCAGC  680
CAGCCTCAGGTCAGCCTGTCTCCCTGAAGAATATCTCCAC  720
AGACACATCGGGTTACTACATCTGTACCTCCAGCAATGAG  760
GAGGGGACGCAGTTCTGCAACATCACGGTGGCCGTCACAT  800
         810       820       830       840
CTCCCTCCATGAACGTGGCCCTGTATGTGGGCATCGCGGT  840
GGGCGTGGTTGCAGCCCTCATTATCATTGGCATCATCATC  880
TACTGCTGCTGCTGCCGAGGGAAGGACGACAACACTGAAG  920
ACAAGGAGGATGCAAGGCCGAACCGGGAAGCCTATGAGGA  960
GCCACCAGAGCAGCTAAGAGAACTTTCCAGAGAGGGAG   1000
        1010      1020      1030      1040
GAGGAGGATGACTACAGGCAAGAAGAGCAGAGGAGCACTG  1040
GGCGTGAATCCCCGGACCACCTCGACCAGTGACAGGCCAG  1080
CAGCAGAGGGCGGCGGAGGAAGGGTTAGGGGTTCATTCTC  1120
CCGCTTCCTGGCCTCCCTTCTCCTTTCTAAGCCCTGTTCT  1160
CCTGTCCCTCCATCCCAGACATTGATGGGGACATTTCTTC  1200
```

FIG. 16B

```
      1210       1220       1230       1240
CCCAGTGTCAGCTGTGGGGAACATGGCTGGCCTGGTAAGG  1240
GGGTCCCTGTGCTGATCCTGCTGACCTCACTGTCCTGTGA  1280
AGTAACCCCTCCTGGCTGTGACACCTGGTGCGGGCCTGGC  1320
CCTCACTCAAGACCAGGCTGCAGCCTCCACTTCCCTCGTA  1360
GTTGGCAGGAGCTCCTGGAAGCACAGCGCTGAGCATGGGG  1400
      1410       1420       1430       1440
CGCTCCCACTCAGAACTCTCCAGGGAGGCGATGCCAGCCT  1440
TGGGGGGTGGGGGCTGTCCTGCTCACCTGTGTGCCCAGCA  1480
CCTGGAGGGGCACCAGGTGGAGGGTTTGCACTCCACACAT  1520
CTTTCTTGAATGAATGAAAGAATAAGTGAGTATGCTTGGG  1560
CCCTGCATTGGCCTGGCCTCCAGCTCCCACTCCCTTTCCA  1600
      1610       1620       1630       1640
ACCTCACTTCCCGTAGCTGCCAGTATGTTCCAAACCCTCC  1640
TGGGAAGGCCACCTCCCACTCCTGCTGCACAGGCCCTGGG  1680
GAGCTTTTGCCCACACACTTTCCATCTCTGCCTGTCAATA  1720
TCGTACCTGTCCCTCCAGGCCCATCTCAAATCACAAGGAT  1760
TTCTCTAACCCTATCCTAATTGTCCACATACGTGGAAACA  1800
      1810       1820       1830       1840
ATCCTGTTACTCTGTCCCACGTCCAATCATGGGCCACAAG  1840
GCACAGTCTTCTGAGCGAGTGCTCTCACTGTATTAGAGCG  1880
CCAGCTCCTTGGGGCAGGGCCTGGGCCTCATGGCTTTTGC  1920
TTTCCCTGAAGCCCTAGTAGCTGGCGCCCATCCTAGTGGG  1960
CACTTAAGCTTAATTGGGGAAACTGCTTTGATTGGTTGTG  2000
      2010       2020       2030       2040
CCTTCCCTTCTCTGGTCTCCTTGAGATGATCGTAGACACA  2040
GGGATGATTCCCACCCAAACCCACGTATTCATTCAGTGAG  2080
TTAAACACGAATTGATTTAAAGTGAACACACACAAGGGAG  2120
CTTGCTTGCAGATGGTCTGAGTTCTTGTGTCCTGGTAATT  2160
CCTCTCCAGGCCAGAATAATTGGCATGTCTCCTCAACCCA  2200
      2210       2220       2230       2240
CATGGGGTTCCTGGTTGTTCCTGCATCCCGATACCTCAGC  2240
CCTGGCCCTGCCCAGCCCATTTGGGCTCTGGTTTTCTGGT  2280
GGGNCTGTCCTGCTGCCCTCCCACNAGCCTCCTTCTGTTT  2320
GTCGAGCATTTCTTCTACTCTTGAGAGCTCAGGCAGCGTT  2360
AGGGCTGCTTAGGTCTCATGGACCAGTGGCTGGTCTCACC  2400
      2410       2420       2430       2440
CAACTGCAGTTTACTATTGCTATCTTTTCTGGATGATCAG  2440
AAAAATAATTCCATAAATCTATTGTCTACTTGCGATTTTT  2480
TAAAAAATGTATATTTTTATATATATTGTTAAATCCTTTG  2520
CTTCATTCCAAATGCTTTCAGTAATAATAAAATTGTGGGT  2560
GGAAA  2565
```

FIG. 17

```
Human: MVGKMMPVLWTLCAVRVTVDAISVETPQDVLRASQGKSVTLPCTYHTSTSSREG
Mouse:        LGKAGSVVWMLCAIWVAADALTVETTQDILRAARGRSVTLPCTYNTYVSDREG LIQWDKLLLTHTERVVIWPFSNKNYIHGELYKNRVSISNNAEQSDASITIDQLT
       FIQWDKLLRSQTERVVTWNFVTKKYIYGNRYENRVRVSNDAELSNASITIDQLT MADNGTYECSVSLMSDLEGNTKSRVRLLLVLVPPSKPECGIEGETIIGNNIQLTC
       MDDNGTYECSVSLMSDQDVNAKSRVRLLVLVPPSKPDCSIQGEMVIGNNIQLTC QSKEGSPTPQYSWKRYNILNQEQPLAQPASGQPVSLKNISTDTSGYYICTSSNE
       HSAEGSPSPQYSWKSYNAQNQQRPLTQPVSGEPLLLKNISTETAGYYICTSSND EGTQFCNITVAVRSPSMNVALYVGIAVGVVAALIIIGIIIYCCCCRGKDDNTED
       VGIESCNITVAPRPPSMNIALYAGIAGSVFVALIIIGVIVYCCCCREKDDKDQD KEDARPNREAYEEPPEQLRELSREREEEDDYRQEEQRSTGRESPDHLDQ
       REDARPNRAAYQVPKKEQKEISRGREDEDDHRHEDRWSSGRSTPDQPFQ
```

1M Tris ph 7.5

1M Hydroxylamine pH 7.5

5,712,369

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
( A ) LENGTH: 38 amino acids
( B ) TYPE: amino acid
( D ) TOPOLOGY: linear ( x i ) SEQUENCE DESCRIPTION: SEQ ID NO: 1:

```
Xaa  Ser  Val  Glu  Thr  Pro  Gln  Asp  Val  Leu  Arg  Ala  Ser  Gln  Gly  Lys
                      5                        10                        15

Ser  Val  Thr  Leu  Pro  Xaa  Thr  Tyr  His  Thr  Ser  Xaa  Xaa  Xaa  Arg  Glu
                     20                        25                        30

Gly  Leu  Ile  Gln  Trp  Asp
                     35
```

( 2 ) INFORMATION FOR SEQ ID NO: 2:

( i ) SEQUENCE CHARACTERISTICS:
( A ) LENGTH: 11 amino acids
( B ) TYPE: amino acid
( D ) TOPOLOGY: linear ( x i ) SEQUENCE DESCRIPTION: SEQ ID NO: 2:

```
Glu  Ala  Tyr  Glu  Glu  Pro  Pro  Glu  Gln  Leu  Arg
                      5                        10
```

( 2 ) INFORMATION FOR SEQ ID NO: 3:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO: 3:

```
Val  Val  Ile  Trp  Pro  Phe  Ser  Asn  Lys
                      5
```

( 2 ) INFORMATION FOR SEQ ID NO: 4:

( i ) SEQUENCE CHARACTERISTICS:
( A ) LENGTH: 40 amino acids
( B ) TYPE: amino acid
( D ) TOPOLOGY: linear ( x i ) SEQUENCE DESCRIPTION: SEQ ID NO: 4:

Ile Ser Val Glu Thr Pro Gln Asp Val Leu Arg Ala Ser Gln Gly Lys
                 5                  10                 15

Ser Val Thr Leu Pro Xaa Thr Tyr His Thr Ser Thr Ser Ser Arg Glu
                20              25                 30

Gly Leu Ile Gln Trp Asp Lys Leu
           35              40

( 2 ) INFORMATION FOR SEQ ID NO: 5:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO: 5:

Asp Val Leu Arg Ala Ser Gln Gly Lys Ser Val Thr Leu Pro Cys Thr
                 5                  10                 15

Tyr His Thr Ser Thr Ser Ser Arg Glu Gly Leu Ile Gln Trp
                20              25                 30

( 2 ) INFORMATION FOR SEQ ID NO: 6:

( i ) SEQUENCE CHARACTERISTICS:
        ( A ) LENGTH: 39 amino acids
        ( B ) TYPE: amino acid
        ( D ) TOPOLOGY: linear ( x i ) SEQUENCE DESCRIPTION: SEQ ID NO: 6:

Asp Lys Leu Leu Leu Thr His Thr Glu Arg Val Val Ile Trp Pro Phe
                 5                  10                 15

Ser Asn Lys Asn Tyr Ile His Gly Glu Leu Tyr Lys Asn Arg Val Ser
                20              25                 30

Ile Ser Asn Asn Ala Glu Gln
           35

( 2 ) INFORMATION FOR SEQ ID NO: 7:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO: 7:

Glu Leu Tyr Lys Asn Arg Val Ser Ile Ser Asn Asn Ala Glu Gln
                 5                  10                 15

( 2 ) INFORMATION FOR SEQ ID NO: 8:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO: 8:

Asp Xaa Gly Thr Tyr Glu Cys Ser Val Ser Leu Met
                 5                  10

( 2 ) INFORMATION FOR SEQ ID NO: 9:

( i ) SEQUENCE CHARACTERISTICS:
        ( A ) LENGTH: 16 amino acids
        ( B ) TYPE: amino acid
        ( D ) TOPOLOGY: linear -continued (xi) SEQUENCE DESCRIPTION: SEQ ID NO: 9:

Ile Gln Leu Thr Cys Gln Ser Lys Glu Gly Ser Pro Thr Pro Gln Tyr
                  5                  10                    15

(2) INFORMATION FOR SEQ ID NO: 10:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO: 10:

Leu Val Leu Val Pro Pro Ser Lys Pro Glu Cys Gly Ile Glu Gly Glu
                  5                  10                    15

Thr Ile Ile Gly Asn
              20

(2) INFORMATION FOR SEQ ID NO: 11:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO: 11:

Ile Leu Asn Gln Glu Gln Pro Leu Ala Gln Pro Ala Ser Gly Gln Pro
                  5                  10                    15

Val (2) INFORMATION FOR SEQ ID NO:12:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 12:

ARYTTRTCCC ACTGAAT                               17

(2) INFORMATION FOR SEQ ID NO:13:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 13:

ARYTTRTCCC ATTGAAT                               17

(2) INFORMATION FOR SEQ ID NO:14:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 14:

ARYTTRTCCC ACTGGAT                               17

(2) INFORMATION FOR SEQ ID NO:15:

(i) SEQUENCE CHARACTERISTICS:
        (A) LENGTH: 17 nucleotides ( B ) TYPE: nucleic acid
( C ) STRANDEDNESS: single
( D ) TOPOLOGY: linear ( x i ) SEQUENCE DESCRIPTION: SEQ ID NO: 15:

ARYTTRTCCC ATTGGAT 17

( 2 ) INFORMATION FOR SEQ ID NO:16:

( i ) SEQUENCE CHARACTERISTICS:
( A ) LENGTH: 17 nucleotides
( B ) TYPE: nucleic acid
( C ) STRANDEDNESS: single
( D ) TOPOLOGY: linear ( x i ) SEQUENCE DESCRIPTION: SEQ ID NO: 16:

ARYTTRTCCC ACTGTAT 17

( 2 ) INFORMATION FOR SEQ ID NO:17:

( i ) SEQUENCE CHARACTERISTICS:
( A ) LENGTH: 17 nucleotides
( B ) TYPE: nucleic acid
( C ) STRANDEDNESS: single
( D ) TOPOLOGY: linear ( x i ) SEQUENCE DESCRIPTION: SEQ ID NO: 17:

ARYTTRTCCC ATTGTAT 17

( 2 ) INFORMATION FOR SEQ ID NO:18:

( i ) SEQUENCE CHARACTERISTICS:
( A ) LENGTH: 17 nucleotides
( B ) TYPE: nucleic acid
( C ) STRANDEDNESS: single
( D ) TOPOLOGY: linear ( x i ) SEQUENCE DESCRIPTION: SEQ ID NO: 18:

CGAGGTCGAC GGTATCG 17

( 2 ) INFORMATION FOR SEQ ID NO:19:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( x i ) SEQUENCE DESCRIPTION: SEQ ID NO: 19:

CCTGTCTGGA GGCTGCCAGT 20

( 2 ) INFORMATION FOR SEQ ID NO:20:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( x i ) SEQUENCE DESCRIPTION: SEQ ID NO: 20:

AGGTGCAGGG CAGGGTGACA 20

( 2 ) INFORMATION FOR SEQ ID NO:21:

( i ) SEQUENCE CHARACTERISTICS:
( A ) LENGTH: 11 nucleotides
( B ) TYPE: nucleic acid
( C ) STRANDEDNESS: single ( D ) TOPOLOGY: linear ( x i ) SEQUENCE DESCRIPTION: SEQ ID NO: 21:

GCCCRCCATG G　　11

( 2 ) INFORMATION FOR SEQ ID NO:22:

( i ) SEQUENCE CHARACTERISTICS:
        ( A ) LENGTH: 319 amino acids
        ( B ) TYPE: amino acid
        ( D ) TOPOLOGY: linear ( x i ) SEQUENCE DESCRIPTION: SEQ ID NO: 22:

```
Met Val Gly Lys Met Trp Pro Val Leu Trp Thr Leu Cys Ala Val Arg
                 5                  10                 15
Val Thr Val Asp Ala Ile Ser Val Glu Thr Pro Gln Asp Val Leu Arg
             20                  25                 30
Ala Ser Gln Gly Lys Ser Val Thr Leu Pro Cys Thr Tyr His Thr Ser
         35                  40                 45
Thr Ser Ser Arg Glu Gly Leu Ile Gln Trp Asp Lys Leu Leu Leu Thr
     50                  55                 60
His Thr Glu Arg Val Val Ile Trp Pro Phe Ser Asn Lys Asn Tyr Ile
 65                  70                 75                 80
His Gly Glu Leu Tyr Lys Asn Arg Val Ser Ile Ser Asn Asn Ala Glu
                 85                  90                 95
Gln Ser Asp Ala Ser Ile Thr Ile Asp Gln Leu Thr Met Ala Asp Asn
             100                 105                110
Gly Thr Tyr Glu Cys Ser Val Ser Leu Met Ser Asp Leu Glu Gly Asn
         115                 120                125
Thr Lys Ser Arg Val Arg Leu Leu Val Leu Val Pro Pro Ser Lys Pro
     130                 135                140
Glu Cys Gly Ile Glu Gly Glu Thr Ile Ile Gly Asn Asn Ile Gln Leu
145                 150                 155                160
Thr Cys Gln Ser Lys Glu Gly Ser Pro Thr Pro Gln Tyr Ser Trp Lys
                 165                 170                175
Arg Tyr Asn Ile Leu Asn Gln Glu Gln Pro Leu Ala Gln Pro Ala Ser
             180                 185                190
Gly Gln Pro Val Ser Leu Lys Asn Ile Ser Thr Asp Thr Ser Gly Tyr
         195                 200                205
Tyr Ile Cys Thr Ser Ser Asn Glu Glu Gly Thr Gln Phe Cys Asn Ile
     210                 215                220
Thr Val Ala Val Arg Ser Pro Ser Met Asn Val Ala Leu Tyr Val Gly
225                 230                 235                240
Ile Ala Val Gly Val Val Ala Ala Leu Ile Ile Ile Gly Ile Ile Ile
                 245                 250                255
Tyr Cys Cys Cys Cys Arg Gly Lys Asp Asp Asn Thr Glu Asp Lys Glu
             260                 265                270
Asp Ala Arg Pro Asn Arg Glu Ala Tyr Glu Glu Pro Pro Glu Gln Leu
         275                 280                285
Arg Glu Leu Ser Arg Glu Arg Glu Glu Glu Asp Asp Tyr Arg Gln Glu
     290                 295                300
Glu Gln Arg Ser Thr Gly Arg Glu Ser Pro Asp His Leu Asp Gln
305                 310                 315
```

( 2 ) INFORMATION FOR SEQ ID NO:23:

( i ) SEQUENCE CHARACTERISTICS:

(A) LENGTH: 960 nucleotides
(B) TYPE: nucleic acid
(C) STRANDEDNESS: single
(D) TOPOLOGY: linear (xi) SEQUENCE DESCRIPTION: SEQ ID NO: 23:

| | | | | | | |
|---|---|---|---|---|---|---|
| ATGGTGGGGA | AGATGTGGCC | TGTGTTGTGG | ACACTCTGTG | CAGTCAGGGT | GACCGTCGAT | 60 |
| GCCATCTCTG | TGGAAACTCC | GCAGGACGTT | CTTCGGGCTT | CGCAGGGAAA | GAGTGTCACC | 120 |
| CTGCCCTGCA | CCTACCACAC | TTCCACCTCC | AGTCGAGAGG | GACTTATTCA | ATGGGATAAG | 180 |
| CTCCTCCTCA | CTCATACGGA | AAGGGTGGTC | ATCTGGCCGT | TTTCAAACAA | AAACTACATC | 240 |
| CATGGTGAGC | TTTATAAGAA | TCGCGTCAGC | ATATCCAACA | ATGCTGAGCA | GTCCGATGCC | 300 |
| TCCATCACCA | TTGATCAGCT | GACCATGGCT | GACAACGGCA | CCTACGAGTG | TTCTGTCTCG | 360 |
| CTGATGTCAG | ACCTGGAGGG | CAACACCAAG | TCACGTGTCC | GCCTGTTGGT | CCTCGTGCCA | 420 |
| CCCTCCAAAC | CAGAATGCGG | CATCGAGGGA | GAGACCATAA | TTGGGAACAA | CATCCAGCTG | 480 |
| ACCTGCCAAT | CAAAGGAGGG | CTCACCAACC | CCTCAGTACA | GCTGGAAGAG | GTACAACATC | 540 |
| CTGAATCAGG | AGCAGCCCCT | GGCCCAGCCA | GCCTCAGGTC | AGCCTGTCTC | CCTGAAGAAT | 600 |
| ATCTCCACAG | ACACATCGGG | TTACTACATC | TGTACCTCCA | GCAATGAGGA | GGGGACGCAG | 660 |
| TTCTGCAACA | TCACGGTGGC | CGTCAGATCT | CCCTCCATGA | ACGTGGCCCT | GTATGTGGGC | 720 |
| ATCGCGGTGG | GCGTGGTTGC | AGCCCTCATT | ATCATTGGCA | TCATCATCTA | CTGCTGCTGC | 780 |
| TGCCGAGGGA | AGGACGACAA | CACTGAAGAC | AAGGAGGATG | CAAGGCCGAA | CCGGGAAGCC | 840 |
| TATGAGGAGC | CACCAGAGCA | GCTAAGAGAA | CTTTCCAGAG | AGAGGGAGGA | GGAGGATGAC | 900 |
| TACAGGCAAG | AAGAGCAGAG | GAGCACTGGG | CGTGAATCCC | CGGACCACCT | CGACCAGTGA | 960 |

(2) INFORMATION FOR SEQ ID NO:24:

(i) SEQUENCE CHARACTERISTICS:
(A) LENGTH: 17 nucleotides
(B) TYPE: nucleic acid
(C) STRANDEDNESS: single
(D) TOPOLOGY: linear (xi) SEQUENCE DESCRIPTION: SEQ ID NO: 24:

TGACAAAGAA ATACATC                                                        17

(2) INFORMATION FOR SEQ ID NO:25:

(i) SEQUENCE CHARACTERISTICS:
(A) LENGTH: 17 nucleotides
(B) TYPE: nucleic acid
(C) STRANDEDNESS: single
(D) TOPOLOGY: linear (xi) SEQUENCE DESCRIPTION: SEQ ID NO: 25:

TCTGGCTTGG AGGGTGG                                                        17

(2) INFORMATION FOR SEQ ID NO:26:

(i) SEQUENCE CHARACTERISTICS:
(A) LENGTH: 123 nucleotides
(B) TYPE: nucleic acid
(C) STRANDEDNESS: single
(D) TOPOLOGY: linear (xi) SEQUENCE DESCRIPTION: SEQ ID NO: 26:

| | | | | | | |
|---|---|---|---|---|---|---|
| AGTATCTAAC | GAGTGCTGAG | GTTGTCAAAT | GCTGACCATG | GACGACAATG | GCACCTACGA | 60 |
| GTGCTCCGGT | GTCACTGATG | GCCTCTATCA | CCATCGACCA | TCGGACCAGG | ATGTCAACGC | 120 |
| CAA | | | | | | 123 |

( 2 ) INFORMATION FOR SEQ ID NO:27:

( i ) SEQUENCE CHARACTERISTICS:
        ( A ) LENGTH: 120 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 27:

```
AGTATCTAAC GATGCTGAGT TGTCAAATGC CTCTATCAGC TGACCATGGA CGACAATGGC      60
ACCTACGAGT GCTCCGTGTC ACTGATGCCA TCGACCATCG GACCAGGATG TCAACGCCAA     120
```

( 2 ) INFORMATION FOR SEQ ID NO:28:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO: 28:

```
Tyr Glu Asn Arg Val Arg Val Ser Asn Asp Ala Glu Lys Ser Asn
                 5                  10                  15
Ala Ser Ile Thr Ile Asp Gln Lys Thr Met Asp Asp Asn Gly Thr
                20                  25                  30
Tyr Glu Cys Ser Val Ser Leu Met Ser Asp Gln
                35                  40
```

( 2 ) INFORMATION FOR SEQ ID NO:29:

( i ) SEQUENCE CHARACTERISTICS:
        ( A ) LENGTH: 2565 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 29:

```
GGGACTCCAG TTGGGCCAGG CCAGAAGCTG CTGTAGCTTT AACCAGACAG CTCAGACCTG      60
TCTGGAGGCT GCCAGTGACA GGTTAGGTTT AGGGCAGAGA AGAAGCAAGA CCATGGTGGG     120
GAAGATGTGG CCTGTGTTGT GGACACTCTG TGCAGTCAGG GTGACCGTCG ATGCCATCTC     180
TGTGGAAACT CCGCAGGACG TTCTTCGGGC TTCGCAGGGA AAGAGTGTCA CCCTGCCCTG     240
CACCTACCAC ACTTCCACCT CCAGTCGAGA GGGACTTATT CAATGGGATA AGCTCCTCCT     300
CACTCATACG GAAAGGGTGG TCATCTGGCC GTTTTCAAAC AAAAACTACA TCCATGGTGA     360
GCTTTATAAG AATCGCGTCA GCATATCCAA CAATGCTGAG CAGTCCGATG CCTCCATCAC     420
CATTGATCAG CTGACCATGG CTGACAACGG CACCTACGAG TGTTCTGTCT CGCTGATGTC     480
AGACCTGGAG GGCAACACCA AGTCACGTGT CCGCCTGTTG GTCCTCGTGC CACCCTCCAA     540
ACCAGAATGC GGCATCGAGG GAGAGACCAT AATTGGGAAC AACATCCAGC TGACCTGCCA     600
ATCAAAGGAG GGCTCACCAA CCCCTCAGTA CAGCTGGAAG AGGTACAACA TCCTGAATCA     660
GGAGCAGCCC CTGGCCCAGC CAGCCTCAGG TCAGCCTGTC TCCCTGAAGA ATATCTCCAC     720
AGACACATCG GGTTACTACA TCTGTACCTC CAGCAATGAG GAGGGGACGC AGTTCTGCAA     780
CATCACGGTG GCCGTCAGAT CTCCCTCCAT GAACGTGGCC CTGTATGTGG GCATCGCGGT     840
GGGCGTGGTT GCAGCCCTCA TTATCATTGG CATCATCATC TACTGCTGCT GCTGCCGAGG     900
GAAGGACGAC AACACTGAAG ACAAGGAGGA TGCAAGGCCG AACCGGGAAG CCTATGAGGA     960
GCCACCAGAG CAGCTAAGAG AACTTTCCAG AGAGAGGGAG GAGGAGGATG ACTACAGGCA    1020
```

| | | | | | | |
|---|---|---|---|---|---|---|
| AGAAGAGCAG | AGGAGCACTG | GGCGTGAATC | CCCGGACCAC | CTCGACCAGT | GACAGGCCAG | 1080 |
| CAGCAGAGGG | CGGCGGAGGA | AGGGTTAGGG | GTTCATTCTC | CCGCTTCCTG | GCCTCCCTTC | 1140 |
| TCCTTTCTAA | GCCCTGTTCT | CCTGTCCCTC | CATCCCAGAC | ATTGATGGGG | ACATTTCTTC | 1200 |
| CCCAGTGTCA | GCTGTGGGGA | ACATGGCTGG | CCTGGTAAGG | GGGTCCCTGT | GCTGATCCTG | 1260 |
| CTGACCTCAC | TGTCCTGTGA | AGTAACCCCT | CCTGGCTGTG | ACACCTGGTG | CGGGCCTGCC | 1320 |
| CTCACTCAAG | ACCAGGCTGC | AGCCTCCACT | TCCCTCGTAG | TTGGCAGGAG | CTCCTGGAGA | 1380 |
| GCACAGCGCT | GAGCATGGGG | CGCTCCCACT | CAGAACTCTC | CAGGGAGGCG | ATGCCAGCCT | 1440 |
| TGGGGGGTGG | GGGCTGTCCT | GCTCACCTGT | GTGCCCAGCA | CCTGGAGGGG | CACCAGGTGG | 1500 |
| AGGGTTTGCA | CTCCACACAT | CTTTCTTGAA | TGAATGAAAG | AATAAGTGAG | TATGCTTGGG | 1560 |
| CCCTGCATTG | GCCTGGCCTC | CAGCTCCCAC | TCCCTTTCCA | ACCTCACTTC | CCGTAGCTGC | 1620 |
| CAGTATGTTC | CAAACCCTCC | TGGGAAGGCC | ACCTCCCACT | CCTGCTGCAC | AGGCCCTGGG | 1680 |
| GAGCTTTTGC | CCACACACTT | TCCATCTCTG | CCTGTCAATA | TCGTACCTGT | CCCTCCAGGC | 1740 |
| CCATCTCAAA | TCACAAGGAT | TTCTCTAACC | CTATCCTAAT | TGTCCACATA | CGTGGAAACA | 1800 |
| ATCCTGTTAC | TCTGTCCCAC | GTCCAATCAT | GGGCCACAAG | GCACAGTCTT | CTGAGCGAGT | 1860 |
| GCTCTCACTG | TATTAGAGCG | CCAGCTCCTT | GGGGCAGGGC | CTGGGCCTCA | TGGCTTTTGC | 1920 |
| TTTCCCTGAA | GCCCTAGTAG | CTGGCGCCCA | TCCTAGTGGG | CACTTAAGCT | TAATTGGGGA | 1980 |
| AACTGCTTTG | ATTGGTTGTG | CCTTCCCTTC | TCTGGTCTCC | TTGAGATGAT | CGTAGACACA | 2040 |
| GGGATGATTC | CCACCCAAAC | CCACGTATTC | ATTCAGTGAG | TTAAACACGA | ATTGATTTAA | 2100 |
| AGTGAACACA | CACAAGGGAG | CTTGCTTGCA | GATGGTCTGA | GTTCTTGTGT | CCTGGTAATT | 2160 |
| CCTCTCCAGG | CCAGAATAAT | TGGCATGTCT | CCTCAACCCA | CATGGGGTTC | CTGGTTGTTC | 2220 |
| CTGCATCCCG | ATACCTCAGC | CCTGGCCCTG | CCCAGCCCAT | TTGGGCTCTG | GTTTCTGGT | 2280 |
| GGGNCTGTCC | TGCTGCCCTC | CCACNAGCCT | CCTTCTGTTT | GTCGAGCATT | TCTTCTACTC | 2340 |
| TTNAGAGCTC | AGGCAGCGTT | AGGGCTGCTT | AGGTCTCATG | GACCAGTGGC | TGGTCTCACC | 2400 |
| CAACTGCAGT | TTACTATTGC | TATCTTTTCT | GGATGATCAG | AAAAATAATT | CCATAAATCT | 2460 |
| ATTGTCTACT | TGCGATTTTT | TAAAAAATGT | ATATTTTAT | ATATATTGTT | AAATCCTTTG | 2520 |
| CTTCATTCCA | AATGCTTTCA | GTAATAATAA | AATTGTGGGT | GGAAA | | 2565 |

ISOLATED PROTEIN WHICH BINDS TO A33 ANTIBODY, AND PEPTIDES CORRESPONDING TO PORTIONS OF THE PROTEIN

CROSS REFERENCE TO RELATED APPLICATIONS

This application is a continuation-in-part of U.S. patent application Ser. No. 08/511,876 filed on Aug. 4, 1995 now abandoned, entitled Colon Cell and Colon Cancer Cell Associated Protein and Peptides, which is incorporated herein by reference.

FIELD OF THE INVENTION

This invention is directed to human colon cell and colon cancer cell associated nucleic acid molecules, protein and peptides. Specifically, the protein and peptides of the invention, which are encoded by the nucleic acid molecules of the invention, are found both in and on the surface of human colon cells and human colon cancer cells, and bind to colon cancer antibodies. The protein, in a monomeric form, has a molecular weight of about 43 kD as determined by SDS gel electrophoresis under non-reducing conditions. This protein, peptide fragments thereof and multimers thereof can be used to develop reagents and methods useful in the diagnosis and treatment of cancer.

BACKGROUND OF THE INVENTION

Colorectal carcinoma is a malignant neoplastic disease. There is a high incidence of colorectal carcinoma in the Western world, particularly in the United States. Tumors of this type often metastasize through lymphatic and vascular channels. Many patients with colorectal carcinoma eventually die from this disease. In fact, it is estimated that 62,000 persons in the United States and 8000 persons in Australia die of colorectal carcinoma annually.

To date, systemic therapies and chemotherapies have been developed for the treatment of colorectal cancer. However, no therapies have exhibited sufficient anti-tumor activity to prolong the survival of colorectal carcinoma patients with metastatic disease, with any degree of reliability. As a result, a need still exists to develop methods for the successful treatment of colorectal carcinoma.

Monoclonal antibody A33 is a murine immunoglobulin that has undergone extensive preclinical analysis and localization studies in patients (see Welt et al., *J. Clin. Oncol.*, 8:1894–1906 (1990), Welt et al., *J. Clin. Oncol.*, 12:1561–1571 (1994). This antibody binds to an antigen found in and on the surface of normal colon cells and colon cancer cells. This antigen is known as the A33 antigen.

In carcinomas originating from the colonic mucosa, the A33 antigen is expressed homogeneously in more than 95% of cases. The A33 antigen has not been detected in a wide range of other normal tissues studied. Its restricted expression defines this system as essentially "organ-specific" (colon, rectum and small bowel).

Immunofluorescence experiments have revealed that mAb A33 is internalized into the macropinosomes of A33 antigen-positive cells in vitro (Daghighian et al., *J. Nuc. Med.*, 1995). In a mouse model, mAb A33 has been found to localize to xenografts of human colon cancer in substantial amounts, and it can be identified in the cytoplasm of transplanted colon cancer cells within the first hour after administration. Rapid tumor localization and high level of antibody uptake by tumors are thought to be related to the following factors: (1) A33 antigen is not secreted, and targeting of mAb A33 to tumor cells is therefore not impeded by shed A33 antigen diffusing from tumor cells to the vascular system; (2) mAb A33 is rapidly internalized into the cell once it binds to A33 antigen on the cell membrane, thereby increasing the amount of cell associated antibody; and (3) some colon cancer cell lines express large amounts of A33 antigen, binding up to 800,000 mAb A33 molecules per cell. Due to these properties, a need exists to isolate, characterize and sequence the A33 antigen, as well as related proteins with similar characteristics.

Many purification protocols typically utilize reduction steps in order to analyze proteins of interest by SDS-gel electrophoresis. In this way, proteins can be identified and monitored more easily. The inventors of the instant application found that surprisingly, by utilizing reducing conditions, they were unable to identify the target A33 protein by Western blotting. Standard techniques had to be changed so as to completely remove reducing steps in order to identify, monitor and characterize the A33 antigen of the invention.

Purification of the A33 antigen has been further complicated by co-migration of other proteins, including actin, to about the same position on one and two dimensional gel electrophoresis. In addition, mAb A33 binds non-specifically to actin. The inventors of the instant application identified the Fc region of the antibody as being responsible for the non-specific binding to actin. Removal of the Fc region has allowed the inventors to prevent actin binding. As actin is not a cell surface antigen as colon carcinoma cells, and is not sensitive to reduction, it became clear to the inventors that actin could not be the target for monoclonal antibody A33.

The difficulty in identifying, isolating and characterizing this antigen is evidenced by the fact that although the existence of the A33 antigen has been known for more than a decade, this is the first successful purification, isolation and sequencing of the antigen.

As described herein, the inventors of the instant application have identified, isolated and characterized the A33 antigen. The inventors have also isolated cDNA encoding the A33 antigen, determined the nucleotide sequence of the cDNA, and deduced the amino acid sequence for the A33 antigen. The A33 antigen, also referred to herein as the A33 protein, can be utilized to develop clinical reagents and methods useful in the prognosis, diagnosis and treatment of cancer and other diseases, in particular, cancers such as colon, rectum, gastric and small bowel mucosa cancer.

SUMMARY OF THE INVENTION

This invention is directed to an isolated protein which is found inside and on the surface of normal human colon cells and human colon cancer cells, as well as to peptide fragments of said protein. The protein and peptides are bound by the A33 colon cancer antibody or by polyclonal antibodies raised against regions of the protein sequence. When analyzed by SDS gel electrophoresis, the isolated protein of the invention has a molecular weight of about 43 kD, when non-reducing conditions are utilized. This invention further relates to nucleic acid molecules encoding said protein, and to the use of said protein, peptides and nucleic acid molecules in the diagnosis and treatment of cancer.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 11 is comprised of FIGS. 11A and 11B.

FIG. 12 represents amino acid sequences of peptide fragments in the A33 antigen;

FIG. 16 is comprised of FIGS. 16A and 16B. FIG. 16A, and its continuation FIG. 16B, represent the 2.6 kb cDNA which encodes the A33 antigen.

DETAILED DESCRIPTION OF THE INVENTION

EXAMPLE 1

Figure 1A:
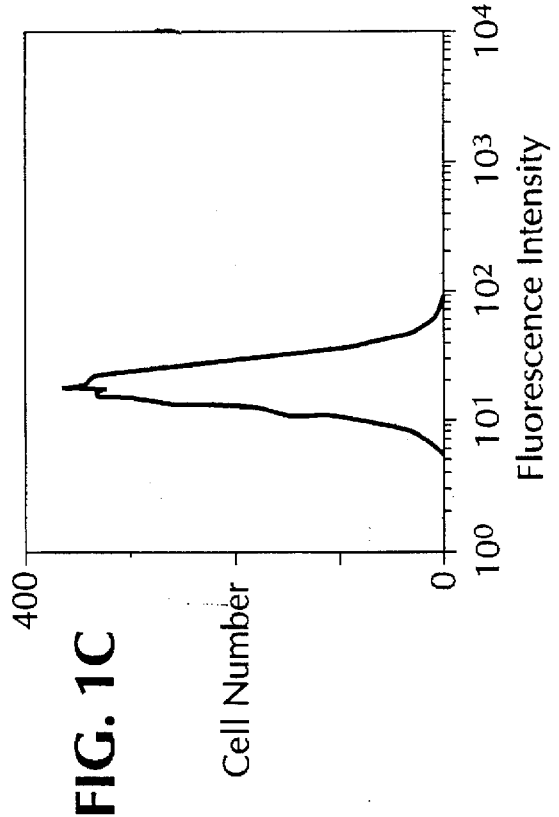
FIG. 1 represents cytofluorographic analysis of the LIM1215 and Hep-2 cells with A33 monoclonal antibody.
Figure 1C:
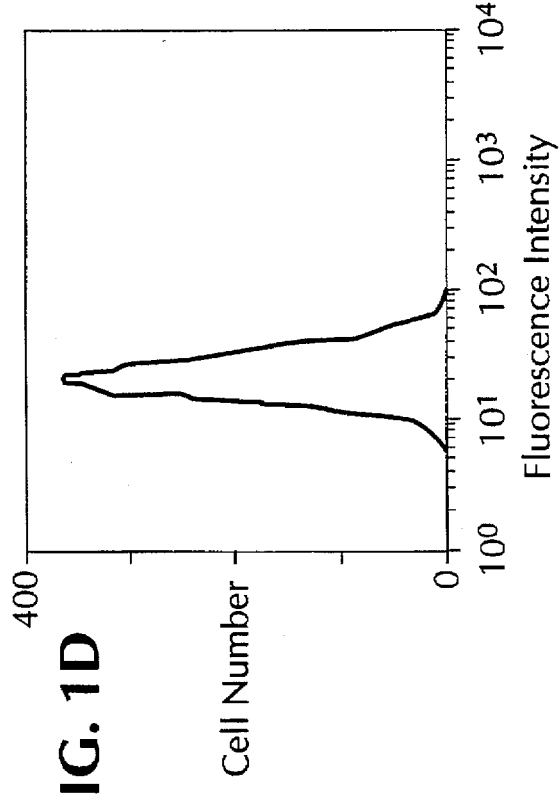
Figure 1B:
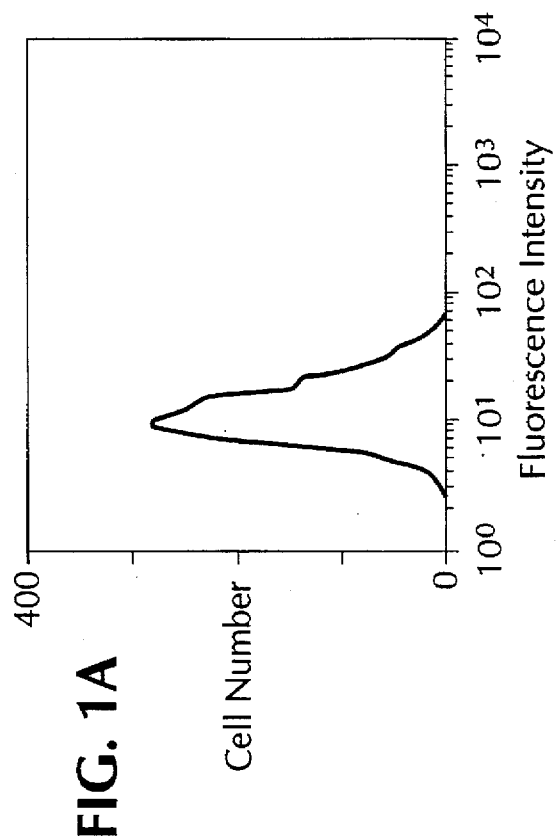
Figure 1D:
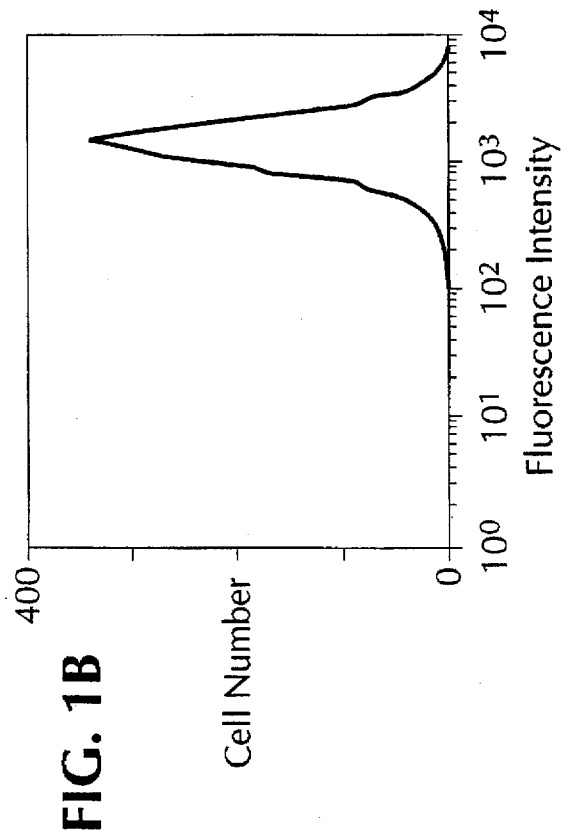

Several colon cancer cultured cell lines, listed in Table 1, were obtained. The LIM1215 cell line was obtained from Ludwig Institute for Cancer Research, Melbourne, Australia. Cell lines SK-CO-17, SK-CO-19, SK-CO-10, SK-CO-11 and SK-CO-15 were obtained from Ludwig Institute for Cancer Research, New York, and Memorial Sloan Kettering Institute, New York. All other cell lines were obtained from the American Type Culture Collection, Rockville, Md.

Using the protocol described by Pfreundschuh et al., *Proc. Natl. Acad. Sci. USA*, 75:5122–5126 (1978), rosetting assays were performed on each of these cell lines using monoclonal antibody A33 (mAb A33), secreted by a hybridoma cell line which was deposited under the Budapest Treaty with the American Type Culture Collection, Rockville, Md. and catalogued as ATCC No. HB 8779. mAb A33 has an isotype of IgG2a and, as described herein, binds to an antigen (protein) denoted A33 which is present in and on the surface of human colon carcinomas. Several of the colon carcinoma cell lines were found to be A33-positive, as determined by rosetting assays, immunoassays and immunohistochemistry (see Table 1, below).

TABLE 1

REACTIVITY OF mAb A33 WITH HUMAN COLON CANCER CELL LINES

| Cell Line | Rosetting A. Titer | Western Blot | Immune precip. |
|---|---|---|---|
| Colon Lines which React with Monoclonal Antibody A33 | | | |
| LIM 1215 | $2^{13}$ | +++ | ++ |
| LOVO | $2^{12}$ | + | |
| LS 174T | $2^{12}$ | | |
| LS 180 | $2^{11}$ | ++ | |
| NCI-H508 | $2^{12}$ | +++ | ++ |
| SK-CO-17 | $2^{9}$ | + | |
| SK-CO-19 | $2^{13}$ | | |
| SNC-2B | $2^{12}$ | | |
| SW403 | $2^{13}$ | + | |
| SW1222 | $2^{12}$ | +++ | ++ |
| COLO 205 | | + | + |
| ASPC-1 (pancreatic) | $2^{13}$ | ++ | ++ |
| Colon Lines which Do not React with Monoclonal Antibody A33 | | | |
| DLD1 | − | | |
| HCT15 | − | − | |
| HT29 | − | − | |
| SK-CO-10 | − | − | |
| SK-CO-11 | | | |
| SK-CO-15 | − | | |
| SW480 | − | | |
| SW620 | − | − | − |
| SW837 | − | | |
| SW1116 | − | − | |
| SW1417 | − | | |

EXAMPLE 2

The LIM1215 colonic cell line, which was positive in the rosetting assays of Example 1, was grown in RPMI medium containing 10% fetal calf serum. Confluent cells ($10^6/cm^2$) were passaged using Trypsin-Versene solution. Cells were seeded 1/10 into tissue culture dishes containing 25 ml RPMI 1640 supplemented with 10% fetal calf serum, 1 µg/ml hydrocortisone, 0.025 U/ml insulin and 10.82 µg/ml α-thioglycerol. Dishes were incubated at 37° C. in an atmosphere of 5% $CO_2$ for 5 days. After removing the media, cells were washed with PBS before being removed from the surface using a cell scraper. Cells were washed in PBS and resuspended at $10^9$ cells/ml.

A33 antigen expression on the surface of the LIM1215 colonic carcinoma cell line was then analyzed by flow cytometry following standard techniques. The Hep-2 epidermoid carcinoma cell line (Boring et al., *Cancer J. Clin.*, Vol. 44, pp. 7–26 (1994)) was used as a negative control. The cells were washed and resuspended at $5 \times 10^6$ cells/ml in 500 µl of PBS containing 5 mM EDTA and 5% fetal calf serum. The cells were incubated with 5 µg A33 mAb for 30 minutes at 4° C. After washing with buffer, the cell/antibody complex was incubated with fluorescein-conjugated anti-murine IgG (1/50 dilution). The negative control was performed by staining the cells with an isotypically matched non-related antibody (5 μg) followed by fluorescein-conjugated anti-murine IgG alone. Flow cytometry was performed using a FACScan flow cytometer (Becton Dickinson, San Jose, Calif., U.S.A.).

FIG. 1 shows cytofluorographic analysis of LIM1215 and Hep-2 cells with A33 monoclonal antibody. The entire population of LIM1215 cells exhibited a strong homogeneous fluorescence (panel B) when incubated with A33 mAb, compared with the fluorescence obtained with the control antibody (panel A). The profiles shown in the panels obtained with the HEP-2 cells (C and D) were overlapping, indicating no detectable A33 mAb binding to these cells. The X axis shows the fluorescence intensity (log scale) and the Y axis shows the cell number.

EXAMPLE 3

Figure 2:
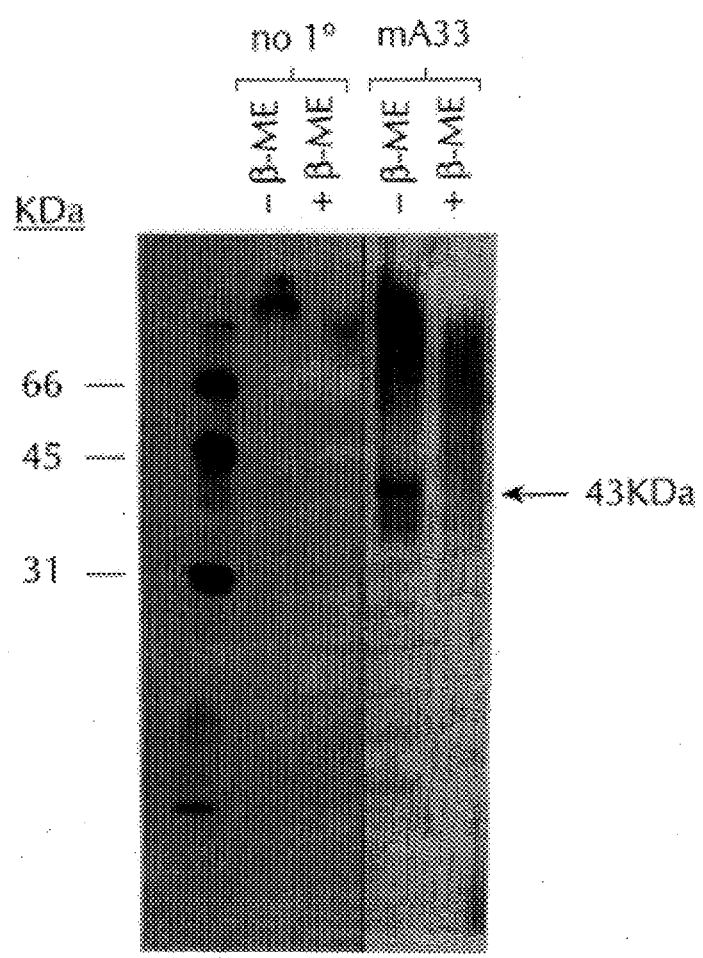
FIG. 2 shows that A33 antigen is detectable by Western blot after SDS gel electrophoresis using non-reducing conditions, but not detectable after SDS gel electrophoresis using reducing conditions. "−B-ME" indicates non-reducing conditions and "+B-ME" refers to reducing conditions.

Cell lines which were A33-positive in rosetting assays (Table 1) were lysed using 0.3% Triton X-100 in PBS pH 7.4. Other detergents known to those skilled in the art can also be used to lyse A33-positive cells. The cell lysates of nine A33-positive cell lines and, in addition, five A33-negative cell lines (controls) were probed for A33 antigen expression by Western blot analysis using normal reducing conditions. A protein with a molecular weight of about 43 kD was detected by Western blotting with mAb A33 in lysates from colon cancer cells which were A33-positive by rosetting assay. This protein was not detected in lysates obtained from cell lines which tested negative for A33 in rosetting assays, or by antibodies other than mAb A33, including anti-actin mAb. The A33 antigen was detectable by Western blot analysis only after SDS gel electrophoresis using non-reducing conditions. The A33 antigen was not detectable using reducing conditions. The Western blot shows in FIG. 2 utilized A33 antigen obtained by affinity purification from SW1222 cells. The upper band (FIG. 2) indicates multimeric form of the A33 protein.

EXAMPLE 4

A33 antigen was immunoprecipitated from colon carcinoma cell lysates. In order to do this, colon cancer cells were labeled with 3H-GlcNAc or $^{35}S$ using standard techniques known to those skilled in the art. Cell lysates which were A33 positive by rosetting assays, and which had a band of about 43 kD by SDS gel electrophoresis under non-reducing conditions, were immunoprecipitated with monoclonal antibody A33.

Figure 3A:
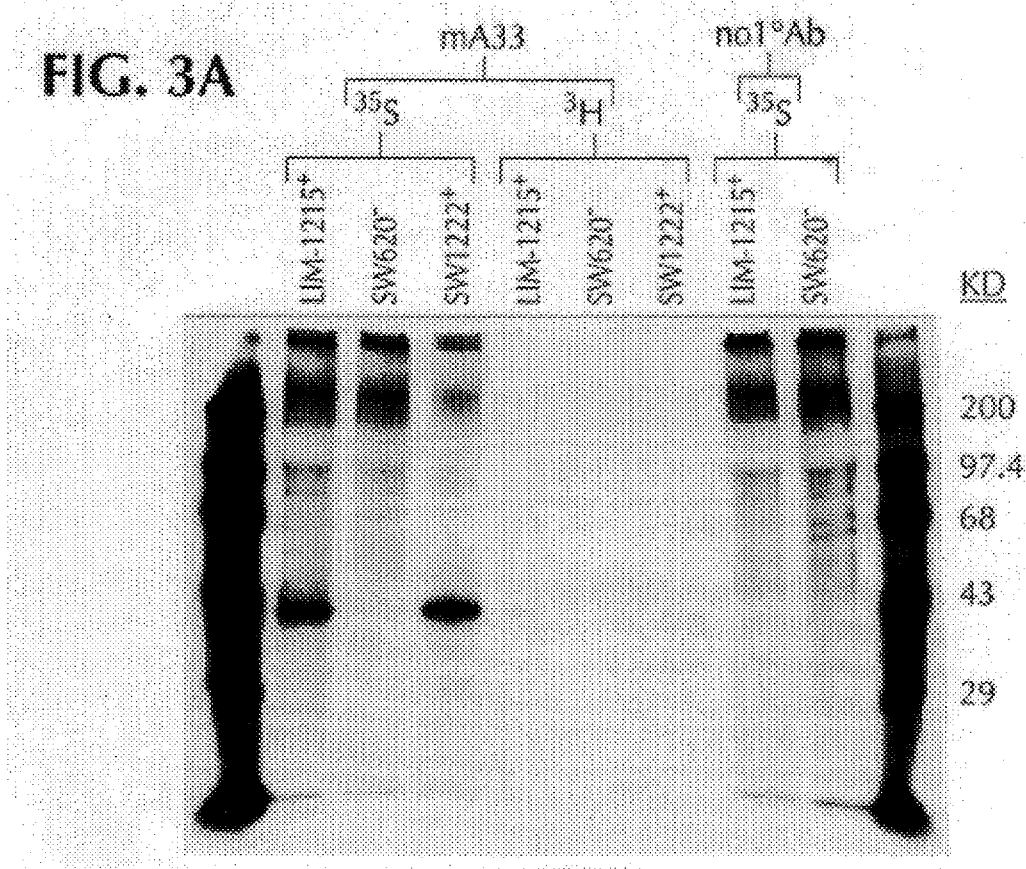
FIG. 3 shows immunoprecipitation of cell lysates with or without mAb A33.
Figure 3B:
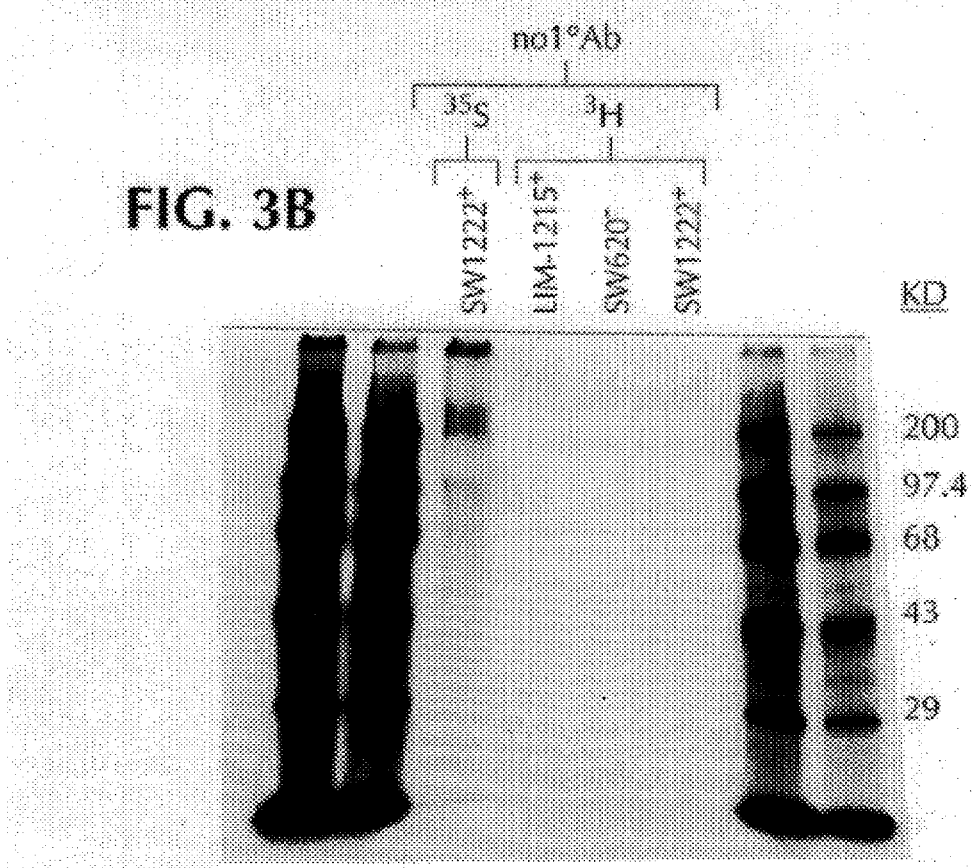

FIG. 3 shows that a molecule was immunoprecipitated from A33-positive lysates which has a molecular weight of about 43 kD. This band was not precipitated by lysates which were A33-negative by rosetting assays. In addition, this band was not precipitated by antibodies other than mAb A33 ("no. 1°Ab" indicates that mAb A33 was not used). Since $^3$H-GlcNAc is a carbohydrate, which is incorporated into the glycosylation side of glycoproteins, these results suggest that the A33 antigen contained in the band is a glycoprotein.

EXAMPLE 5

Figure 4A:
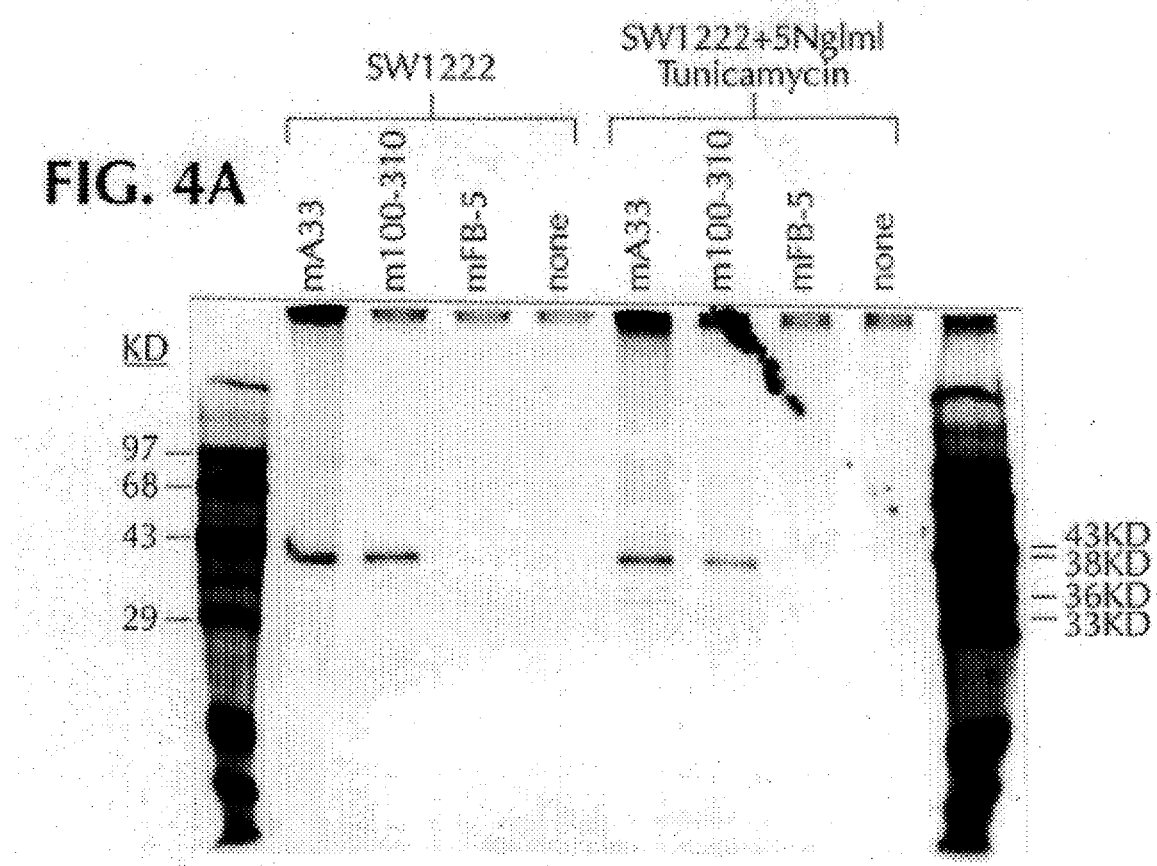
FIG. 4 shows immunoprecipitation of cell lysates which were or were not incubated with tunicamycin.
Figure 4B:
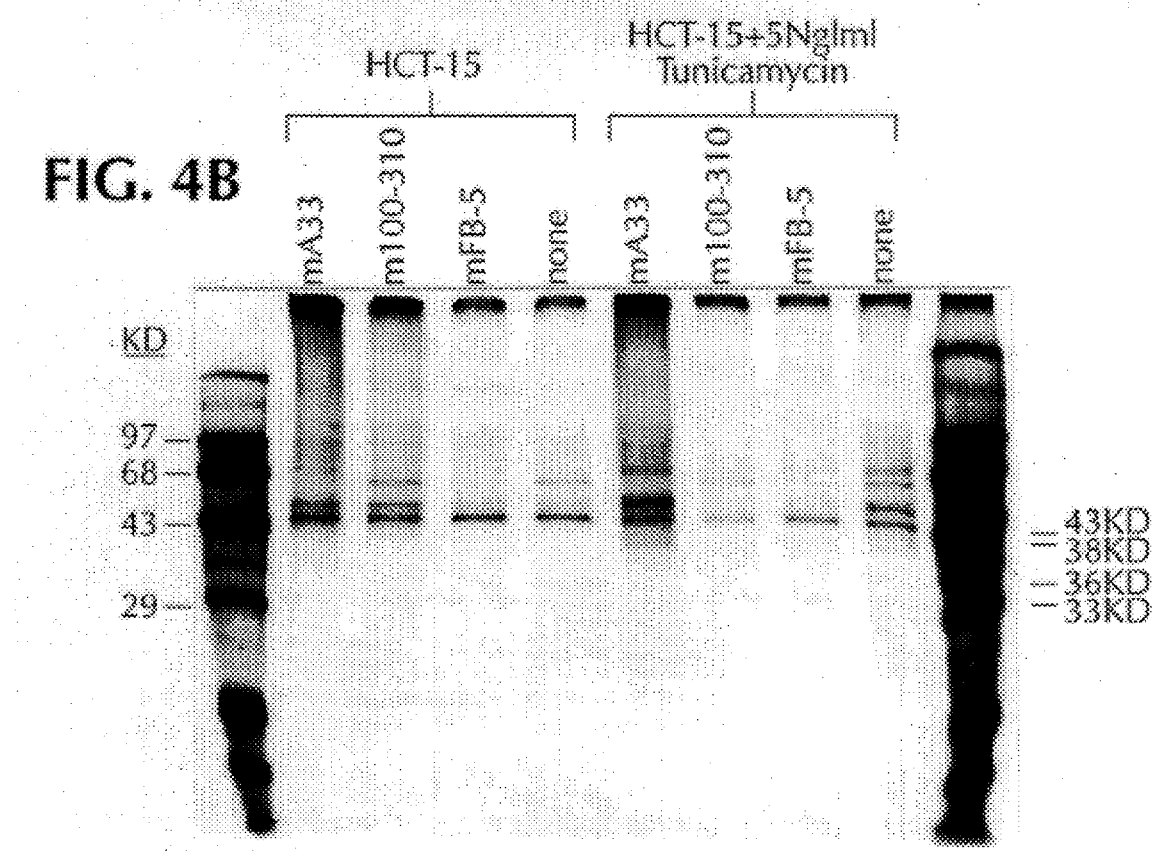

$^{35}$S-labeled SW1222 cells were incubated with 5 μg/ml tunicamycin for 18 hours. Tunicamycin is known to block N-glycosylation of glycoproteins. These cells, as well as cells which were not incubated with tunicamycin, were lysed and subjected to immunoprecipitation with A33 antibody, FB-5 antibody (control) or no antibody (control). FIG. 4 shows the immunoprecipitation results.

Of the cells which were not incubated with tunicamycin, immunoprecipitation with A33 antibody showed a band at about 43 kD. Immunoprecipitation with antibody FB-5, or no antibody, showed no such 43 kD band. Of the cells incubated with tunicamycin, immunoprecipitation with A33 antibody showed a band at 43 kD, as well as three other bands of lower molecular weight. These lower molecular weight bands indicate the presence of A33 antigen with a different degree of glycosylation due to the presence of tunicamycin. This provides further evidence that the A33 antigen is a glycoprotein, and contains N-linked oligosaccharides.

EXAMPLE 6

A33 antigen was identified using 2-dimensional gel electrophoresis under non-reducing conditions. First, the LIM1215 colonic cell line was grown in RPMI medium containing 10% fetal calf serum. Confluent cells ($10^6/cm^2$) were detached from the plastic dish using Trypsin-Versene solution. Cells were seeded 1/10 into tissue culture dishes (150×20 mm) containing 25 ml RPMI 1640 supplemented with 10% fetal calf serum, 1 μg/ml hydrocortisone, 0.024 U/ml insulin and 10.82 μg/ml α-thioglycerol, as described above. Dishes were incubated at 37° C. in an atmosphere of 5% $CO_2$ for 5 days. After removing the media, cells were washed with PBS before being removed from the surface using a cell scraper. Cells were washed in PBS and resuspended at $10^9$ cells/ml.

Next, A33 antigen was extracted from $3×10^8$ LIM1215 cells using 0.3% Triton X-100 in 10 mM Tris-HCl buffer (pH 7.4). The extract was diluted 1:1 with sample buffer comprised of arginine/lysine buffer, pH 10, containing 30% glycerol, and electrophoresed on small (8×8 cm) Novex 2-dimensional gel electrophoresis gels under non-reducing conditions.

Figure 5A:
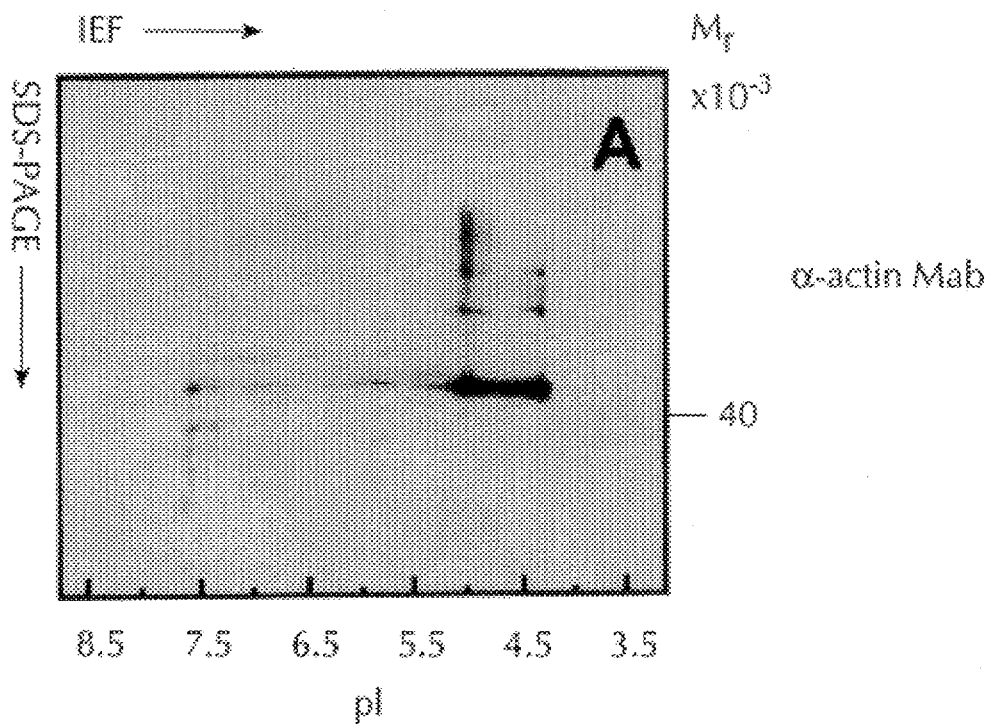
FIG. 5 is comprised of FIGS. 5A and 5B, and represents Western blot analysis of A33 antigen extracted from LIM1215 cells under non-reducing conditions.
Figure 5B:
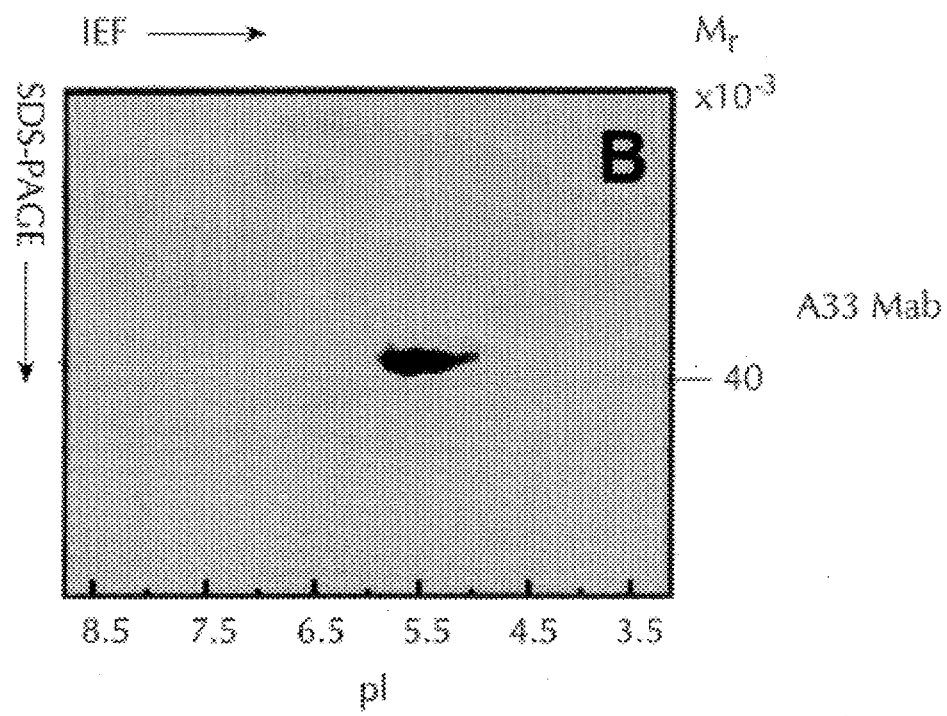

The proteins were separated in the first dimension by isoelectric focusing at a pH of 3.5–8.5, and in the second dimension by SDS-PAGE (10% acrylamide gels). The A33 antigen was localized in the gel by staining with Coomassie Blue R-250, along with immunoblot analysis using mAb A33 (FIG. 5B). For comparison, the staining pattern observed using an anti-actin mAb (FIG. 5A) is shown. Actin is used for comparison because it has similar migration characteristic to the A33 antigen.

EXAMPLE 7

Biosensor analysis was performed on the LIM1215 cell extracts and chromatographic fractions. The extracts and fractions were monitored using an instrumental optical biosensor (BIAcore™, Pharmacia Biosensor, Uppsala, Sweden), with a F(ab)'$_2$ fragment of A33 monoclonal antibody immobilized onto the biosensor surface.

To prepare the F(ab)'$_2$ fragment, A33 antibodies were purified (King et al.; Br. J. Cancer, Vol. 72, pp. 1364–1372 (1995)). F(ab)'$_2$ were generated by pepsin (1% w/w) digestion of 10 mg A33 mAb in 0.1M sodium acetate (pH 3.5). F(ab)'$_2$ were purified by size exclusion chromatography on a Sephacryl S-200 (2.8×60 cm) column (Pharmacia Biotech) equilibrated with 50 mM sodium phosphate (pH 7.4) containing 0.15 mM NaCl. The elution was performed at a flow rate of 0.5 ml/min.

The detection of the antigen binding to the F(ab)'$_2$ fragment is based on the phenomenon of surface plasmon resonance, a technique which measures small changes in refractive index at, or near to, the gold sensor surface. Prior to the biosensor assay, cell extracts and chromatographic fractions were diluted to 100 μl final volume in BIAcore™ buffer (HBS): 10 mM Hepes (pH 7.4) containing 3.4 mM EDTA, 0.15 mM NaCl and 0.005% Tween 20. Samples (30 μl) were injected over the sensor surface at a flow rate of 5 μl/min. Following completion of the injection phase, dissociation was monitored in BIAcore™ buffer at the same flow rate for 360 seconds. Residual bound antigen was eluted and the surface regenerated between injections using 40 μl of 10 mM NaOH. This treatment did not denature the protein immobilized onto the sensor surface as shown by equivalent signals on reinjection of a sample containing the A33 antigen.

Figure 6:
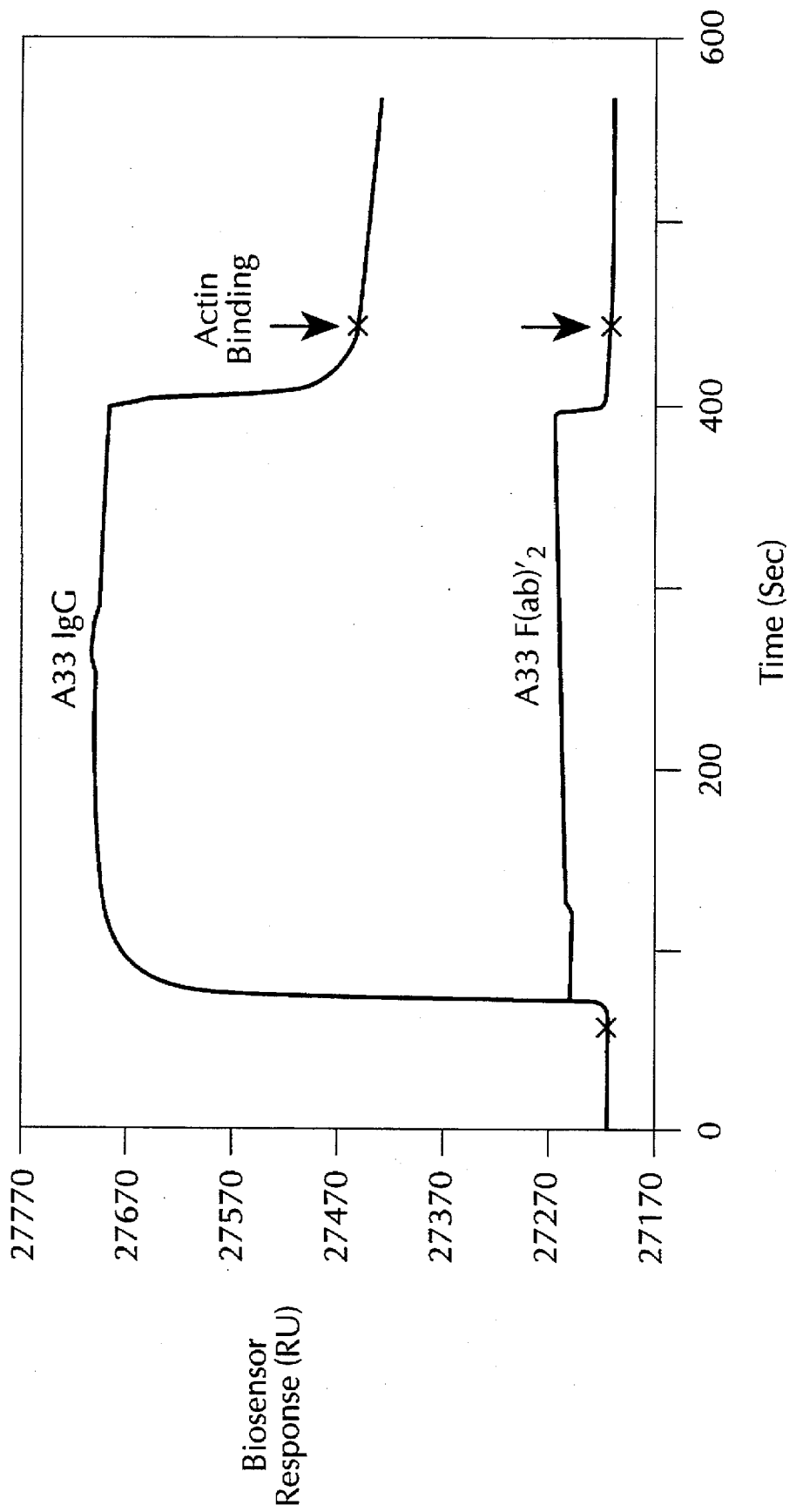
FIG. 6 shows biosensor analysis of the interaction between actin and either A33 IgG or the A33 F(ab)$'_2$ fragment.

FIG. 6 shows biosensor analysis of the interaction between actin and either A33 IgG or the A33 F(ab)'$_2$ fragment. A preparation of rabbit muscle actin (0.3 μg) was injected at a flow rate of 5 μl/min over a sensor surface which had been immobilized with either whole A33 IgG (upper trace) or A33 F(ab)'$_2$ fragment (lower trace). Protein/protein interactions were monitored by surface plasmon resonance. At the end of the injection pulse, a signal of 247 RU was observed due to actin binding to A33 IgG, while the signal corresponding to actin binding to A33 F(ab)'$_2$ was only 4 RU (as indicated by arrows).

EXAMPLE 8

Figure 7:
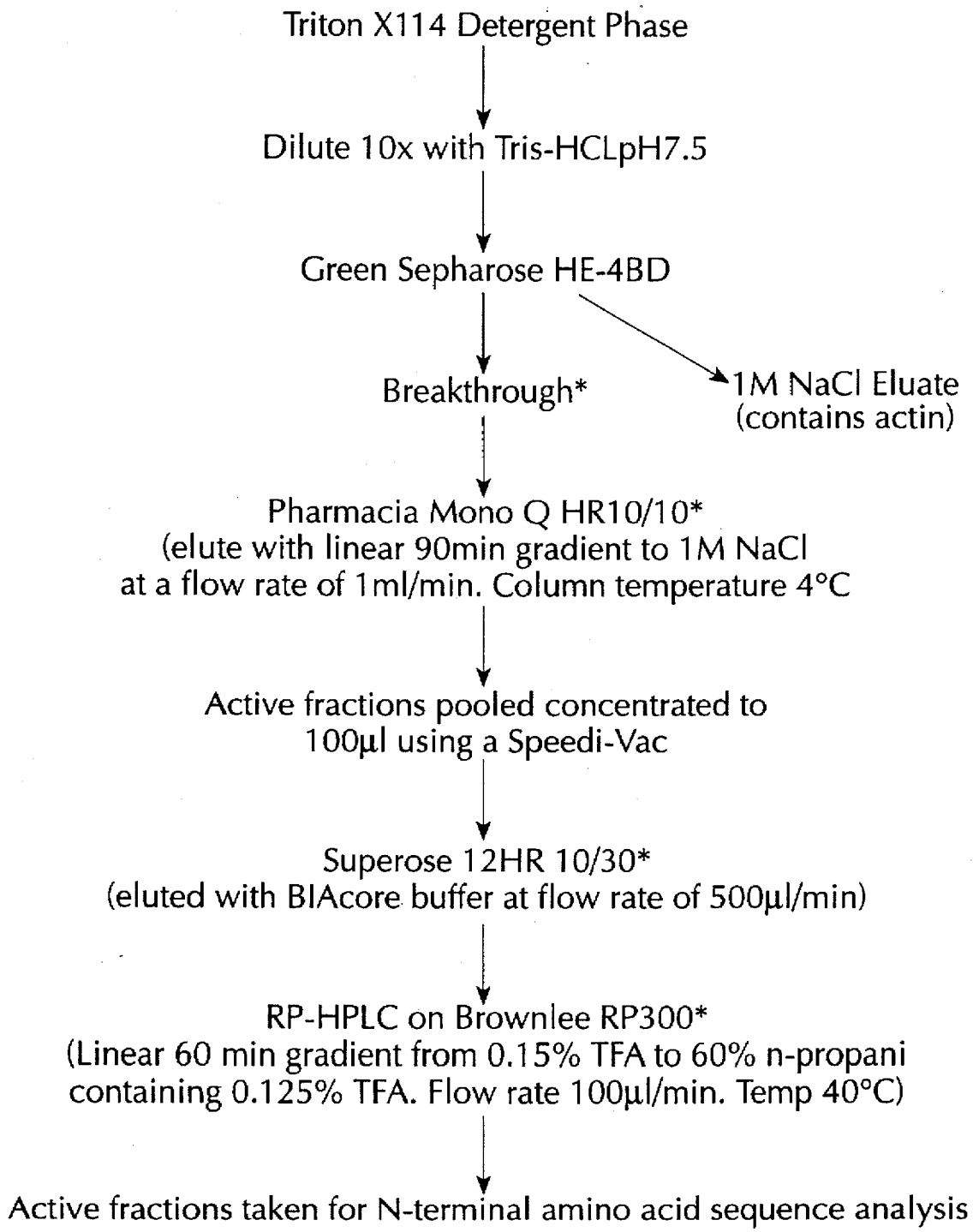
FIG. 7 is a flow chart depicting the chromatographic purification protocol used to purify A33 antigen.

A33 antigen was purified from LIM1215 cells for sequence analysis. FIG. 7 is a flow chart which depicts the chromatographic purification protocol used to purify A33 antigen. To extract A33 antigen, LIM1215 colonic cells (2×10$^9$ cells) were harvested, washed in phosphate-buffered saline (PBS) and solubilized (10$^8$ cells/ml) for 30 minutes at 4° C. with either 0.3% (v/v) Triton X-100 or 1% (v/v) Triton X-114 in 15 mM Tris-HCl (pH 7.4) containing 1 mM PMSF, 1 mM pepstatin, 0.1 mM leupeptin and 0.01 U/ml aprotinin. The resulting extracts were centrifuged twice at 4° C. for 20 minutes at 14,000 g. The Triton-X100 supernatant was taken directly for Green-Sepharose HE-4BD chromatography. The Triton X-114 extracted supernatant was layered over 6% sucrose in 15 mM Tris-HCl (pH 7.4) with 0.06% (v/v) Triton X-114, containing the protease inhibitors listed above. The tubes containing the Triton-X-114 extracts and the sucrose were incubated at 37° C. for 30 minutes and then centrifuged at 25° C. for 15 minutes at 5,000 g. The detergent phase was collected for chromatographic purification.

In order to perform Green-Sepharose chromatography, Triton-X100 extracts or the Triton X-114 detergent phase were diluted to a final concentration of 0.1% Triton and loaded at 4° C. onto a Green-Sepharose HE-4BD column (100×10 mm ID) connected to a Fast Protein Liquid Chromatography system (FPLC, Pharmacia Biotech, Uppsala, Sweden). The column was equilibrated with 10 mM Tris-HCl (pH 7.4) containing 0.1% CHAPS (w/v). Bound proteins, including actin, were eluted stepwise with 1M NaCl. The breakthrough contained the A33 antigen, and was collected for anion-exchange HPLC, as described below.

EXAMPLE 9

Western blot analysis was performed throughout purification to confirm the presence of A33 antigen. Electrophoresis and Western blot analysis were performed on precast Phastgels using a Phastsystem separation and control unit (Pharmacia Biotech). Cell extracts and chromatographic fractions were electrophoresed under non-reducing conditions as described by Reid et al, *Electrophoresis*, Vol. 16, pp. 1120–1130 (1995), on 8–25% SDS-PAGE Phastgels or 8–25% native Phastgels and transferred onto PVDF membranes and incubated with A33 monoclonal antibody. RP-HPLC purified A33 antigen was also analyzed by Western blot under non-reducing and reducing conditions using polyclonal anti-N-terminal peptide antibodies (described herein). IgG binding was probed with horseradish peroxidase-labelled goat anti-mouse IgG, goat anti-human IgG or goat anti-rabbit IgG and detected by enhanced chemiluminescence (ECL).

Figure 8A:
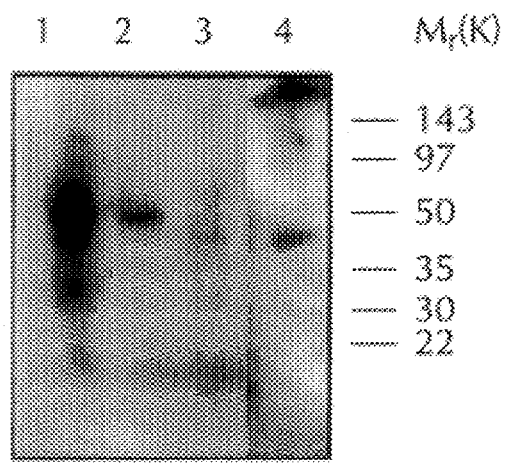
FIG. 8 is comprised of FIGS. 8A and 8B and shows Western blot analysis of Triton X-100 and Triton X-114 extracts of LIM1215 colonic cells, respectively.
Figure 8B:
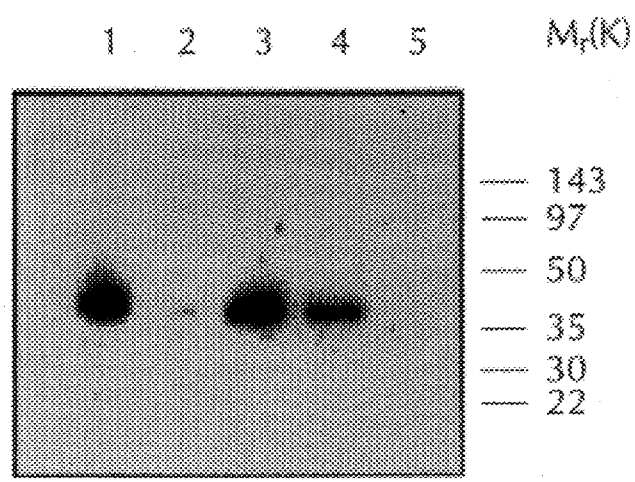

FIG. 8 shows Western blot analysis of the Triton X-100 and Triton X-114 extracts of LIM1215 colonic cells. Panel A shows the following: Lane 1: LIM1215 cells solubilized in 0.3% Triton X-100. Lane 2: Green-Sepharose breakthrough containing the 43K A33 antigen. Lane 3: Green-Sepharose binding proteins eluted with 1M NaCl containing the 41 kD molecular weight band. Lane 4: Rabbit muscle Actin (1 μg).

Panel B shows the following: Lane 1: LIM1215 cells solubilized in 1% Triton X-114. Lane 2: Triton X-114 aqueous phase. Lane 3: Triton X-114 detergent phase. Lane 4: Green-Sepharose breakthrough. Lane 5: Green-Sepharose binding proteins eluted with 1M NaCl.

EXAMPLE 10

Following Green-Sepharose chromatography (described above), anion-exchange HPLC was performed. The Green-Sepharose breakthrough was injected at 4° C. onto a Mono Q HR 10/10 column previously equilibrated in 10 mM Tris-HCl (pH 7.4) containing 0.1% (w/v) CHAPS. The proteins were eluted from the column using a linear 0–1M NaCl gradient generated over 90 minutes at a flow rate of 1 ml/min. Fractions (1 ml) were collected automatically using a fraction collector (FRAC 100, Pharmacia Biotech). Proteins were detected by absorbance at 280 nm. The A33 antigen was detected using both Western blotting under non-reducing conditions and biosensor analysis.

Figure 9:
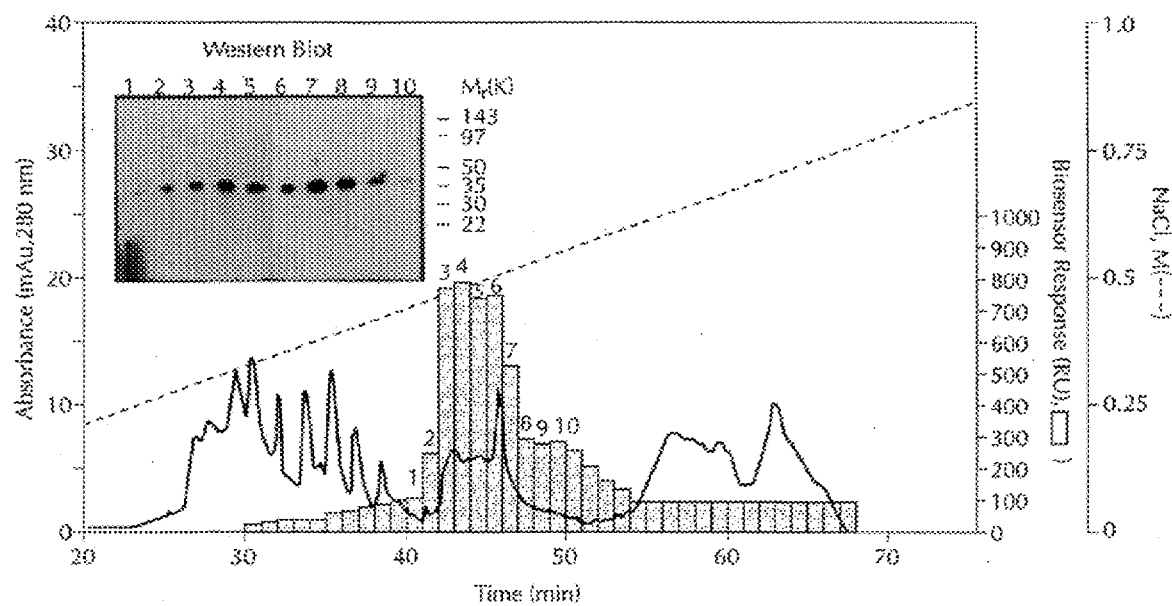
FIG. 9 shows anion-exchange HPLC of the A33 antigen.

FIG. 9 shows anion-exchange HPLC of the A33 antigen. The proteins contained in the Green-Sepharose breakthrough fraction which were loaded onto the Mono Q HR 10/10 anion-exchange column and eluted at a flow rate of 1 ml/min with a linear gradient from 0–1M NaCl are indicated (- - -). One ml fractions were collected and aliquots (20 μl) of each of the fractions were taken for biosensor assay. The approximately 43K antigen was detected in the labelled fractions by Western blot analysis under non-reducing conditions (inset, FIG. 9) as described herein.

EXAMPLE 11

Next, size-exclusion HPLC was performed. The active fractions eluted from the Mono Q column (10 ml) were concentrated 10 fold using a Speed Vac concentrator (Savant Instruments Inc., NY, U.S.A.), dialyzed against PBS containing 0.05% CHAPS (w/v) and loaded at 4° C. onto a Superose 12 HR 10/30 column. Proteins were eluted with PBS containing 0.05% (w/v) CHAPS at a flow rate of 500 μl/min. Fractions (0.5 ml) were collected. Proteins were detected at 280 nm and the A33 antigen was monitored using both Western blotting and biosensor analysis as described above.

Figure 10:
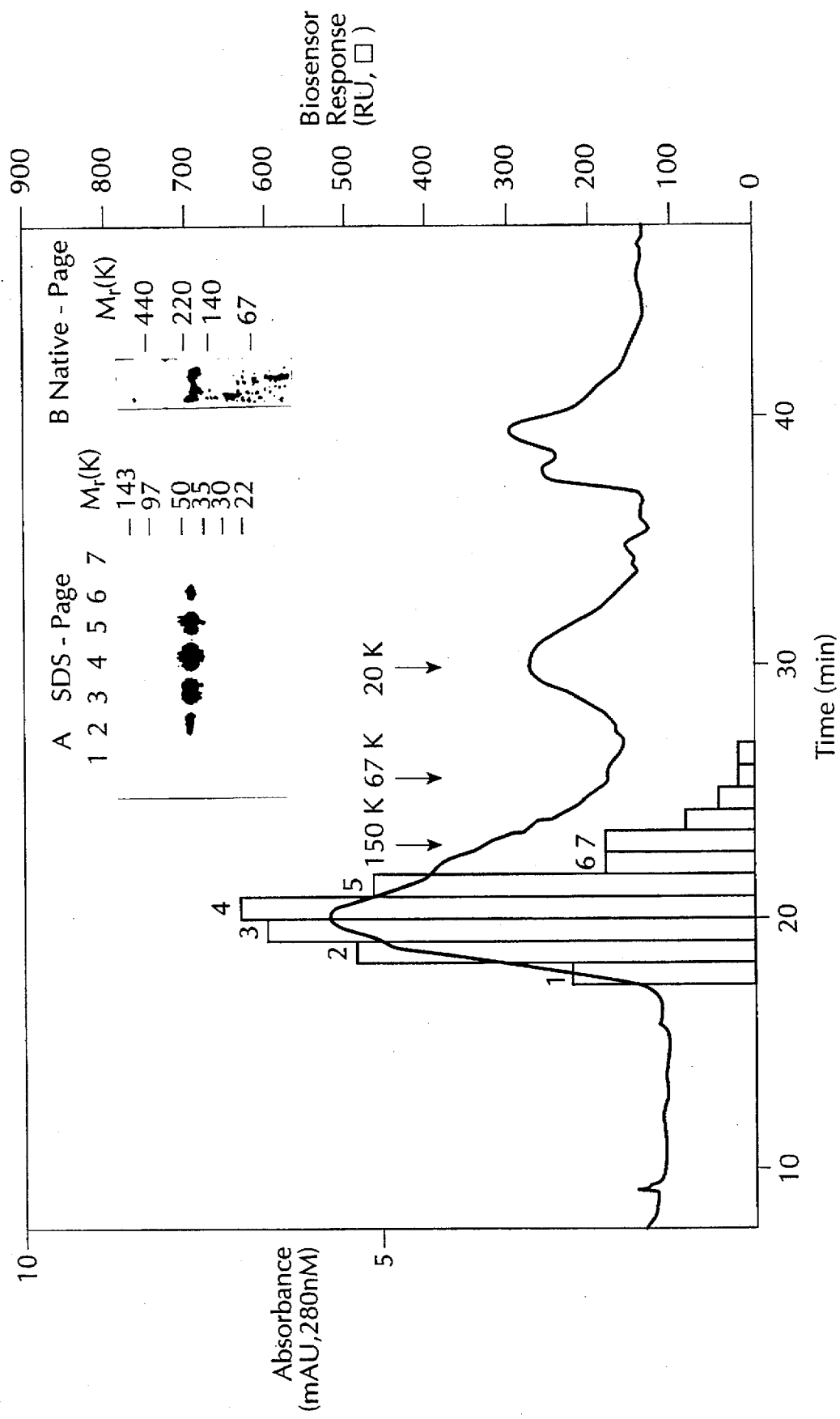
FIG. 10 shows size-exclusion HPLC of the A33 antigen.

FIG. 10 shows size-exclusion HPLC of the A33 antigen. The elution positions of protein calibration standards (BSA dimer, BSA and trypsin inhibitor) are indicated above the chromatographic trace. The A33 antigen was also detected by Western blot analysis under non-reducing conditions (inset A) in the fractions indicated. Immunoblot analysis of a pool of the Superose 12 activity (fractions 2–5) using an 8–25% native gel revealed that the A33 antigen migrated under native conditions (no SDS) with a relative molecular mass of 180 kD (inset B, FIG. 10).

EXAMPLE 12

Reversed-phase HPLC chromatography was then performed. Superose 12 active fractions (2.5 ml) were loaded at a flow rate of 1 ml/min, by multiple 1 ml injections, onto a Brownlee Aquapore RP 300 micropreparative RP-HPLC column (30×2.1 mm ID) equilibrated with the primary solvent, 0.15% (v/v) trifluoroacetic acid (TFA) in water. The proteins were eluted with a linear 60 minute gradient to 60% aqueous n-propanol/0.125% (v/v) TFA at a flow rate of 100 µl/min. The column temperature was 45° C. Protein detection was performed at 215 nm. The A33 antigen was detected using both Western blotting and biosensor analysis. The peak containing the A33 antigen was repurified and further concentrated using a Brownlee Aquapore RP 300 micropreparative RP-HPLC column (100×1 mm ID) prior to N-terminal sequence analysis, using the gradient conditions described above at a flow rate of 50 µl/min. Eluent fractions were recovered manually.

Figure 11A:
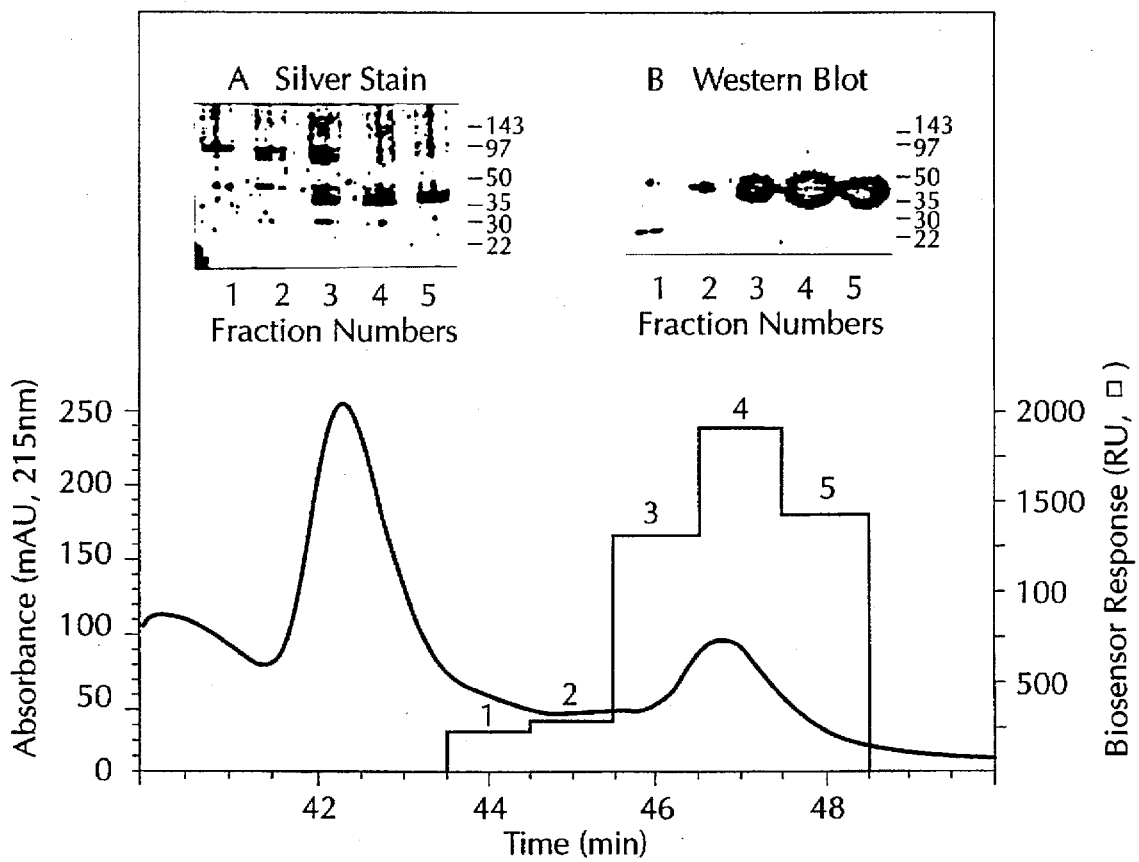
FIG. 11A shows micropreparative RP-HPLC purification of Superose 12 active fractions.
Figure 11B:
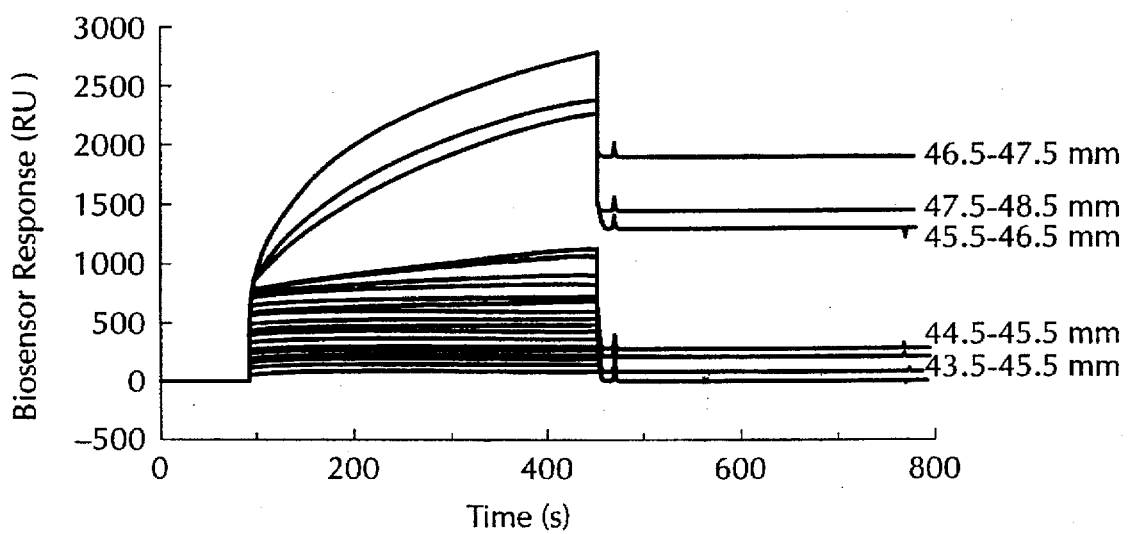
FIG. 11B shows biosensor analysis of the A33 antigen activity in the HPLC fraction.

FIG. 11 shows micropreparative RP-HPLC purification of Superose 12 active fractions. Panel A, main frame, shows the elution profile of the fractions from micropreparative RP-HPLC as analyzed by absorbance at 215 nm and by biosensor. Panel A, inset A, shows aliquots (2 µl) of each fraction, analyzed by SDS-PAGE (8–25% gel, silver stained), and Panel A, inset B, shows a Western blot under non-reducing conditions. Panel B shows biosensor analysis of individual fractions from micropreparative RP-PHLC. Aliquots (20 µl) of each fraction were concentrated using a Speed Vac concentrator and redissolved in 100 µl of BIAcore™ buffer. 30 µl aliquots were analyzed using the biosensor. Activity was found in the fractions eluting between 46 and 48 minutes.

EXAMPLE 13

As discussed above, the A33 antigen-containing reversed-phase HPLC fractions were pooled for amino acid sequence analysis. N-terminal amino acid sequence analysis of purified A33 antigen/protein was performed on a Hewlett-Packard model G1005A protein sensor operated with the routine 3.0 sequencer program described by Reid et al., *Electrophoresis*, Vol. 16, pp. 1120–1130 (1995). The following N-terminus sequence of 38 amino acids was obtained: (SEQ ID NO: 1)

XSVETPQDVLRASQGKSVTLPXTYHTSXXXREGLIQWD.

A search of all of the available protein, DNA and expressed sequence tag databases did not reveal any significant amino acid sequence identity of the A33 N-terminus with known proteins.

In addition, A33 antigen-containing reversed phase HPLC fractions were subjected to tryptic digestion as described by Simpson et al., *Eur. J. Biochem.*, Vol. 183, pp. 715–722 (1989). Peptide fragments T1 and T2 were obtained. The amino acid sequences for these peptide fragments are shown in FIG. 12.

EXAMPLE 14

Figure 13:
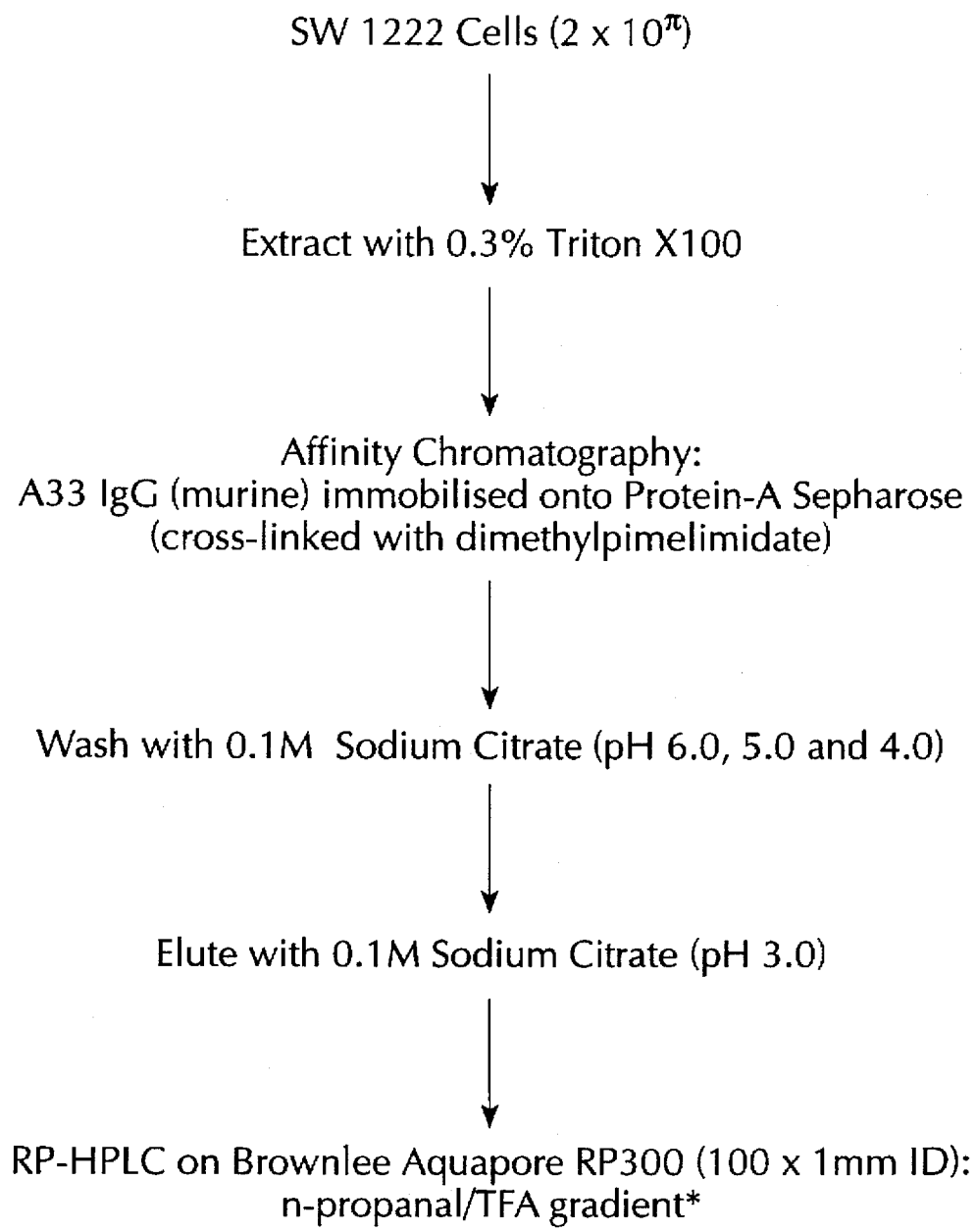
FIG. 13 is a flow chart which shows a protocol used for affinity purification of A33 antigen.

A33 antigen-containing fractions were obtained from SW1222 cells utilizing the protocol shown in FIG. 13. To perform affinity chromatography, the A33 affinity column was prepared according to the protocol described by Schneider et al., *J. Biol. Chem.* Vol. 257, pp. 10766–10769 (1982). A33 monoclonal antibody was diluted to 1 mg/ml in 0.1M borate, pH 8.2, and incubated overnight at 4° C. with 1.5 ml Protein A-Sepharose CLAB. After washing with 0.1M borate, pH 9.2, the Protein-A-monoclonal antibody complex was incubated for 1 hour at room temperature with 20 mM dimethylpimelimidate in 0.1M borate, pH 9.2. Non-covalently bound antibody was removed with 50 mM glycine, pH 2.5. The remaining active dimethylpimelimidate groups were deactivated by washing and incubating the beads with 0.1M ethanolamine pH 8.0.

The reversed-phase HPLC fractions were pooled for amino acid sequence analysis. Sequence analysis was performed as described in Example 13. The following A33 N-terminus sequence was obtained: (SEQ ID NO: 4)

ISVETPQDVLRASQGKSVTLPXTYHTSTSSREGLIQWDKL

A sequence search did not reveal any significant amino acid sequence identity with known proteins. This N-terminus sequence was utilized to obtain the cDNA sequence which encodes A33 antigen (described below).

In addition, A33 antigen-containing reversed phase HPLC fractions were subjected to Asp-N endoproteinase digestion as described by Simpson et al., *Eur. J. Biochem.*, Vol. 183, pp. 715–722 (1989). Peptide fragments D1, D2, D3 and D4 were obtained. These peptides were purified by micropreparative RP-HPLC. The amino acid sequences for these peptide fragments are shown in FIG. 12. It was determined that there was a lack of an amino acid in cycle 3 of the Edman Degradation of peptide D4. Asp 112 was flanked by Thr at position 114. As this is a classical N-glycosylation motif, evidence was provided that A33 protein is N-glycosylated.

Fractions were also subjected to pepsin digestion. Pepsin digests were performed as described by Sarkar et al, *Proc. Nat'l Acad. Sci. U.S.A.*, Vol. 88, pp. 234–238 (1991). Peptide fragment P1 was obtained. The amino acid sequence for peptide fragment P1 is shown in FIG. 12.

RP-HPLC fragments were subjected to Thermolysin/pepsin/Asp-N digestion. Thermolysin digestion was performed as described by Sarkar, supra. Peptide fragments Pc2 and Pc2 were obtained. The amino acid sequences for peptide fragments Pc1 and Pc2 are shown in FIG. 12.

EXAMPLE 15

Immunization studies were performed utilizing an immunogen derived from the amino acid sequence of the N-terminus of A33 antigen. A chemically synthesized peptide, SVETPQDVLRASQGKSVTLP (amino acids 2–21 of SEQ ID NO:1), which corresponds to 20 amino acids in the A33 antigen N-terminus, was conjugated to KLH and injected, with adjuvant, into two mice and into two rabbits. Rabbits were immunized four times at three week intervals. In the first immunization, complete Freund's adjuvant (CFA) was used. In subsequent rabbit immunizations, incomplete Freund's adjuvant (IFA) was used. Mice were immunized four times at two week intervals, using standard adjuvant. Sera were obtained from the rabbits and from the mice. The sera were subjected to Western blot analysis.

Figure 14:
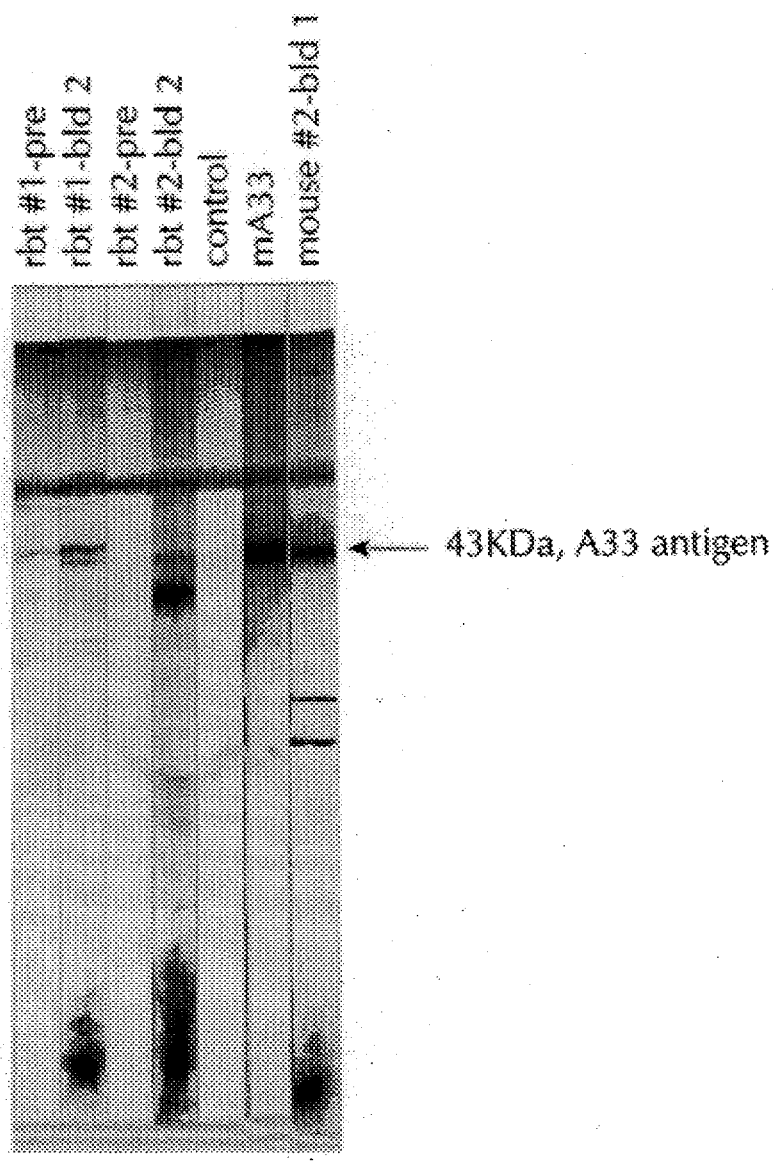
FIG. 14 represents Western blot analysis of sera obtained from mice and rabbits immunized with chemically synthesized peptide SVETPQDVLRASQGKSVTLP (amino acids 2–21 of SEQ ID NO:1) conjugated to keyhole limpet hemocyanin (KLH)
Figure 15:
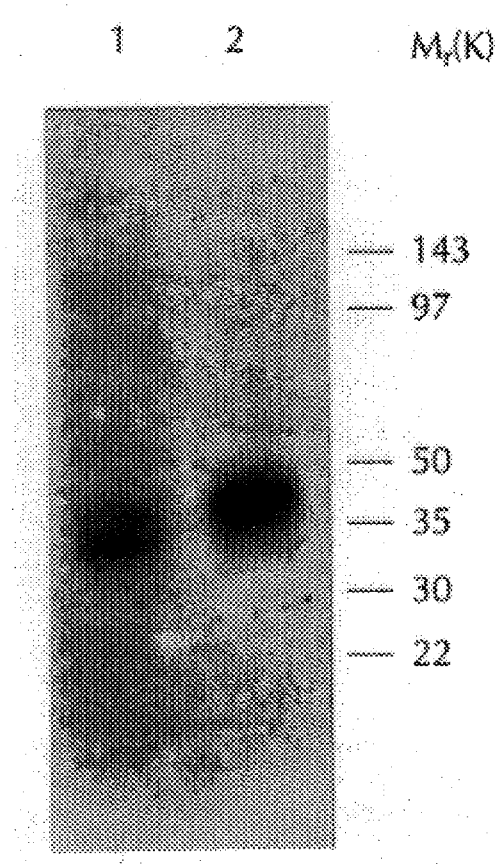
FIG. 15 represents Western blot analysis of the A33 antigen under non-reduced (panel 1) and reduced (panel 2) conditions using an anti-peptide IgG raised against the N-terminus of the A33 antigen.
Figure 18A:
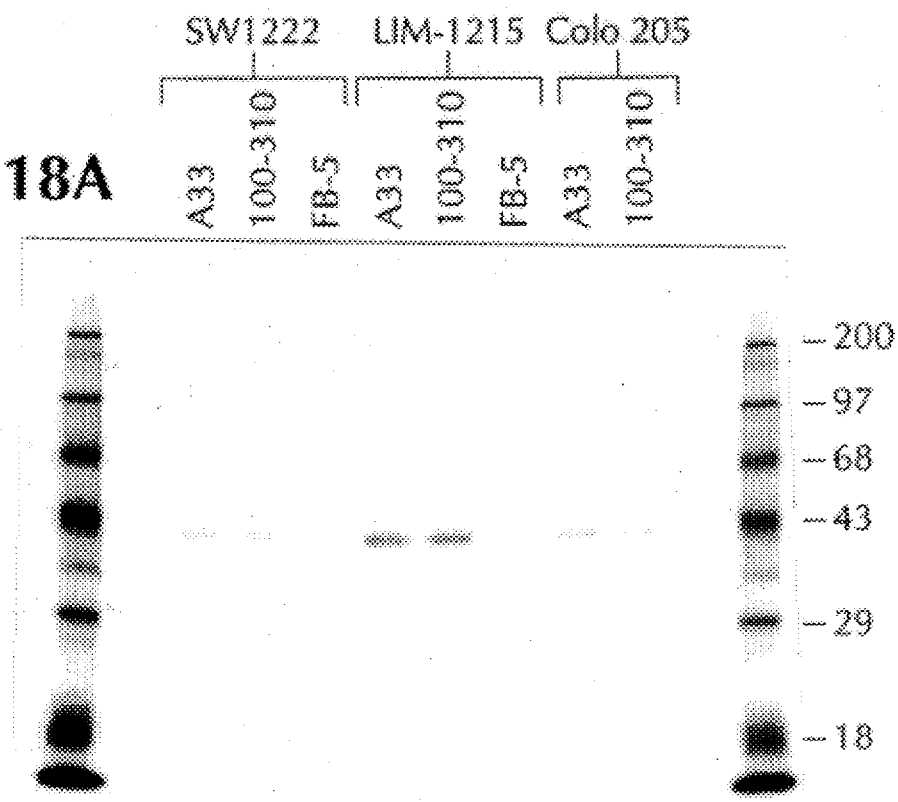
Figure 18B:
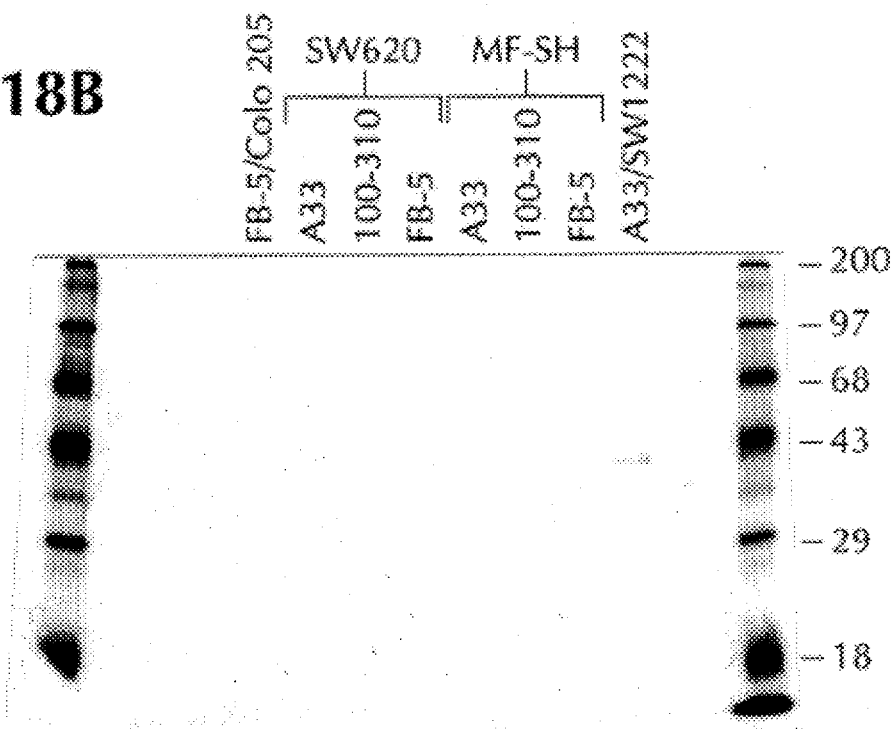
Figure 19A:
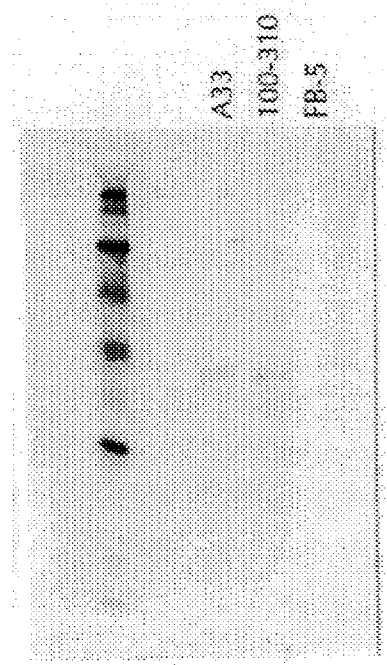
Figure 19B:
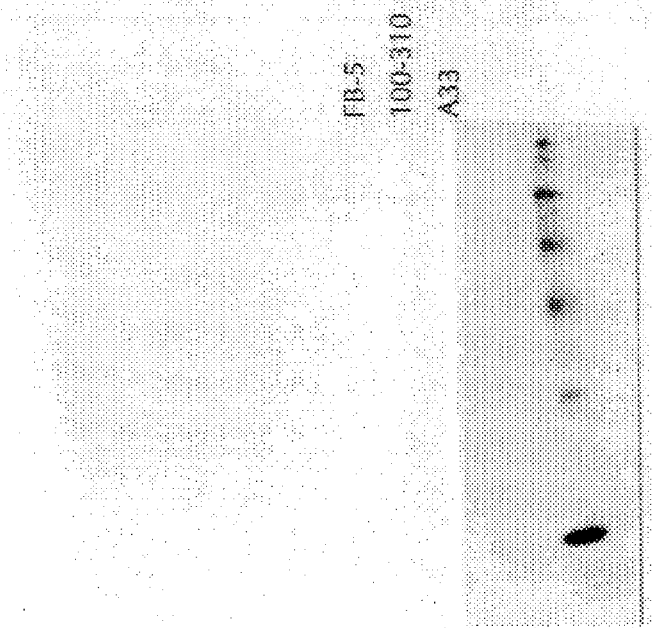

It was found that both the rabbits and mice developed IgG antibodies which reacted with the peptide, and also with the 43 kD band (the same 43 kD band was recognized by mAb A33) in SW1222 ELISA (FIG. 14). IgG was purified from rabbit immune sera by Protein-A affinity chromatography. Purified IgG was characterized by SDS-PAGE and Western blot analysis for reactivity with LIM1215 cell lysates and purified A33 antigen. The IgG was found to react strongly with the 20 amino acid peptide and with the approximately 43 kD protein which was recognized by mAb A33 under non-reducing conditions. In addition, rabbit IgG anti-serum reacted strongly with whole A33 antigen in reduced form (FIG. 15). HPLC purified A33 antigen from LIM1215 (0.1 μg) was electrophoresed on an 8–25% SDS-PAGE Phastgel under non-reducing (FIG. 15, lane 1) and reducing (FIG. 15, lane 2) conditions and analyzed by Western blot using an anti-peptide IgG raised against residues 2–20 of the A33 N-terminal sequence, as described above. The A33 antigen N-terminus sequence, and fragments thereof, can be used to develop A33 antigen-specific antibodies. These antibodies will recognize and bind to A33 antigen or fragments thereof, in either reduced or non-reduced form.

EXAMPLE 16

The amino acid sequence of the A33 N-terminus of A33 protein was used to clone A33 protein cDNA. Poly (A)$^+$ RNA (80 μg) was prepared in house from confluent LIM1215 cells by two rounds of enrichment on columns of oligo (dT) cellulose using standard procedures. From this mRNA, a LIM1215 cDNA library was custom-synthesized in the ξZAPII expression vector by Clontech (Palo Alto, Calif., U.S.A.) using oligo (dT) and random hexamer primers to prime first strand DNA synthesis (standard procedures).

Successful screening of the library was achieved with a DNA probe generated from the LIM1215 cDNA library using the polymerase chain reaction (PCR). Six 17 mer antisense oligonucleotides (R9–R14), each with only 8-fold degeneracy, were designed to correspond to of the A33 antigen N-terminal sequence LIQWDK (amino acids 55–60 SEQ ID NO:22) as follows:

Primer #1477 (R9) 5'A(AG)(CT)TT(AG)TCCCACTGAAT (SEQ ID NO: 12)
Primer #1478 (R10) 5'A(AG)(CT)TT(AG) TCCCATTGAAT (SEQ ID NO: 13)
Primer #1479 (R11) 5'A(AG)(CT)TT(AG) TCCCACTGGAT (SEQ ID NO: 14)
Primer #1480 (R12) 5'A(AG)(CT)TT(AG) TCCCATTGGAT (SEQ ID NO: 15)
Primer #5915 (R13) 5'A(AG)(CT)TT(AG) TCCCACTGTAT (SEQ ID NO: 16)
Primer #5916 (R14) 5'A(AG)(CT)TT(AG)TCCCATTGTAT (SEQ ID NO: 17)

These were paired with sense primers designed to hybridize to sequences present in the backbone of the λZAPII vector and used in PCR reactions with the amplified LIM1215 cDNA library as source of A33 antigen template. This successful reaction occurred with primers described below. For PCR reaction, the template used was amplified LIM1215 cDNA library in λZAPII vector. The primers used were as follows: KS primer 5'CGAGGTCGACGGTATCG (SEQ ID NO:18) (20 mer) (hybridizes to a sequence in multicloning site of λZAPII vector); and R10 primer (described above). The reaction conditions were as follows:

| | |
|---|---|
| cDNA library (10" pfu/ml) | 1 μl |
| 10 × T'aq ™ bufer | 5 μl |
| 2.4 mM NTPs | 4 μl |
| 15 mM MgCl$_2$ | 5 μl |
| KS (50 pmoles/μl) | 1 μl |
| R10 (50 pmoles/μl) | 1 μl |
| Water | 32.5 μl |
| T'aq polymerase | 0.5 μl (added last in Hot |
| | 50.0 μl Start) |

The touchdown program used in the PCR was as follows:

| | |
|---|---|
| 1 | 95° C. × 5 min |
| 2 | 95° C. × 1 min |
| 3 | 60° C. × 1 min |
| | −2° C. in subsequent cycles |
| 4 | 72° C. × 2 min |
| 5 | Go to (2) eleven times |
| 6 | 95° C. × 1 min |
| 7 | 37° C. × 2 min |
| 8 | 72° C. × 2 min |
| 9 | 95° C. × 1 min |
| 10 | 45° C. × 2 min |
| 11 | 72° C. × 2 min |
| 12 | Go to (9) thirteen times |
| 13 | 72° C. × 5 min |
| 14 | 4° C. hold |

Three products were generated, having the sizes 1.4 kb, 0.5 kb, and 0.3 kb.

The 1.4 kb product (designated R10/1) and the 0.5 kb product (designated R10/2) were separated on a 3% agarose gel and purified using the Bresa-clean™ nucleic acid purification kit (Bresatec, Adelaide, S. Australia). These purified products were used as templates in further PCR reactions in order to generate a greater yield of product. PCR reactions were conducted exactly as described above, except that 1 μl of purified PCR product (either R10/1 or R10/2) was used as DNA template instead of 1 μl of the LIM1215 cDNA library.

The R10/1 PCR reaction produced two bands:

Upper band Size 1.4 kb (very faint)

Lower band Size 0.3 kb (strong) designated 10/1 300 bp

The R10/2 PCR reaction produced two bands:

Upper band Size 0.5 kb (strong)

Lower band Size 0.3 kb (strong) designated 10/2

The 0.3 kb fragments (10/1 300 bp and 10/2) were gel-purified as described above. Nucleotide sequencing on both fragments was conducted and the reverse complement of each sequence was found to encode a portion of the A33 N-terminal protein sequence.

The following precise primers to the A33 antigen cDNA sequence were then synthesized in order to amplify a precise 189 bp PCR product for use as a probe to screen the LIM1215 cDNA library.

Primer #1747 (A33 sense primer 1) 5' CCTGTCTGGAGGCTGCCAGT (20mer) (SEQ ID NO: 19)
Primer #1748 (A33 antisense primer 1) 5' AGGTGCAGGGCAGGGTGACA (20mer) (SEQ ID NO: 20)

The above primers were used in a standard PCR reaction as follows, and generated a product of the predicted size (189 bp).

Standard PCR Reaction Conditions

| | |
|---|---|
| 10/1-300 bp product | 1 µl |
| 10 × T'aq buffer | 2 µl |
| 2.5 mM NTPs | 1.6 µl |
| 15 mM MgCl$_2$ | 2 µl |
| Primer #1747 (50 pmoles/µl) | 1 µl |
| Primer #1748 (50 pmoles/µl) | 1 µl |
| Water | 11 µl |
| T'aq polymerase | 0.4 µl (added last) |
| | 20.0 µl |

Standard PCR program as follows:

| | |
|---|---|
| 1 | 95° C. × 5 min |
| 2 | 95° C. × 1 min |
| 3 | 55° C. × 1 min |
| 4 | 72° C. × 1 min |
| 5 | Go to (2) thirty times |
| 6 | 72° C. × 5 min |
| 7 | 4° C. hold |

The 189 bp product was separated on a 3% agarose gel and purified using the Bresa-clean™ kit. It was then radio-labelled with [α$^{32}$P]ATP and [α$^{32}$P]CTP to a specific activity of >10$^7$ dpm/µg DNA using the random primers reaction and Klenow polymerase (standard procedures) and used to screen 800,000 clones of the LIM1215 cDNA library (standard procedures). After three rounds of screening thirteen purified A33 antigen cDNA clones were obtained, the longest of which were approximately 2.6 kb.

The labelled PCR probe was also used in Northern analysis and produced a strong hybridizing signal with a single species of mRNA of size approximately 2.6 kb in total RNA and poly (A)$^+$ enriched RNA from LIM1215 cells, suggesting that the 2.6 kb clones were likely to be close to full-length. Several clones were sequenced and all were found to encode the A33 antigen N-terminal protein sequence. The complete nucleotide sequence of the 2.6 kb clone (clone 11) is depicted in FIG. 16.

When one 2.6 kb cDNA clone was radiolabelled as described above (i.e., using [α$^{32}$P]ATP and [α$^{32}$P]CTP in the random primers reaction with Klenow polymerase) and used in Northern analysis, a strong signal of size approximately 2.6 kb was obtained with total RNA prepared from A33 antigen positive cell lines (LIM1215, LIM1899 and LIM1863) and normal human colonic epithelial tissue, but not with total RNA form A33 antigen negative cell lines (LIM2099, LIM2405, LIM2537). This is consistent with the hypothesis that the 2.6 kb clones are full-length, and encode the A33 antigen.

The 2.6 kb translation protein product (A33 antigen) was deduced from the 2.6 kb cDNA. It was predicted that protein translation is initiated at the second ATG from the 5' end in the cDNA sequence. This was deduced by reference to the Kozak consensus sequence (GCCC(A/G) CC<u>ATG</u>G) for initiation of translation. The deduced full length translation protein product is comprised of 319 amino acids, and has the following amino acid sequence (SEQ ID NO: 22)

| Met | Val | Gly | Lys | Met 5 | Trp | Pro | Val | Leu | Trp 10 | Thr | Leu | Cys | Ala | Val 15 | Arg |
|---|---|---|---|---|---|---|---|---|---|---|---|---|---|---|---|
| Val | Thr | Val | Asp 20 | Ala | Ile | Ser | Val | Glu 25 | Thr | Pro | Gln | Asp | Val 30 | Leu | Arg |
| Ala | Ser | Gln 35 | Gly | Lys | Ser | Val | Thr 40 | Leu | Pro | Cys | Thr | Tyr 45 | His | Thr | Ser |
| Thr | Ser 50 | Ser | Arg | Glu | Gly | Leu 55 | Ile | Gln | Trp | Asp | Lys 60 | Leu | Leu | Leu | Thr |
| His 65 | Thr | Glu | Arg | Val | Val 70 | Ile | Trp | Pro | Phe | Ser 75 | Asn | Lys | Asn | Tyr | Ile 80 |
| His | Gly | Glu | Leu | Tyr 85 | Lys | Asn | Arg | Val | Ser 90 | Ile | Ser | Asn | Asn | Ala 95 | Glu |
| Gln | Ser | Asp | Ala 100 | Ser | Ile | Thr | Ile | Asp 105 | Gln | Leu | Thr | Met | Ala 110 | Asp | Asn |
| Gly | Thr | Tyr 115 | Glu | Cys | Ser | Val | Ser 120 | Leu | Met | Ser | Asp | Leu 125 | Glu | Gly | Asn |
| Thr | Lys 130 | Ser | Arg | Val | Arg | Leu 135 | Leu | Val | Leu | Val | Pro 140 | Pro | Ser | Lys | Pro |
| Glu 145 | Cys | Gly | Ile | Glu | Gly 150 | Glu | Thr | Ile | Ile | Gly 155 | Asn | Asn | Ile | Gln | Leu 160 |
| Thr | Cys | Gln | Ser | Lys 165 | Glu | Gly | Ser | Pro | Thr 170 | Pro | Gln | Tyr | Ser | Trp 175 | Lys |
| Arg | Tyr | Asn | Ile 180 | Leu | Asn | Gln | Glu | Gln 185 | Pro | Leu | Ala | Gln | Pro 190 | Ala | Ser |
| Gly | Gln | Pro 195 | Val | Ser | Leu | Lys | Asn 200 | Ile | Ser | Thr | Asp | Thr 205 | Ser | Gly | Tyr |
| Try | Ile 210 | Cys | Thr | Ser | Ser | Asn 215 | Glu | Glu | Gly | Thr | Gln 220 | Phe | Cys | Asn | Ile |
| Thr 225 | Val | Ala | Val | Arg | Ser 230 | Pro | Ser | Met | Asn | Val 235 | Ala | Leu | Tyr | Val | Gly 240 |
| Ile | Ala | Val | Gly | Val 245 | Val | Ala | Ala | Leu | Ile 250 | Ile | Ile | Gly | Ile | Ile 255 | Ile |
| Tyr | Cys | Cys | Cys 260 | Cys | Arg | Gly | Lys | Asp 265 | Asp | Asn | Thr | Glu | Asp 270 | Lys | Glu |
| Asp | Ala | Arg 275 | Pro | Asn | Arg | Glu | Ala 280 | Tyr | Glu | Glu | Pro | Pro 285 | Glu | Gln | Leu |
| Arg | Glu | Leu | Ser | Arg | Glu | Arg | Glu | Glu | Glu | Asp | Asp | Tyr | Arg | Gln | Glu |

|     | 290 |     |     |     |     | 295 |     |     |     |     | 300 |     |     |     |
|-----|-----|-----|-----|-----|-----|-----|-----|-----|-----|-----|-----|-----|-----|-----|
| Glu | Gln | Arg | Ser | Thr | Gly | Arg | Glu | Ser | Pro | Asp | His | Leu | Asp | Gln |
| 305 |     |     |     |     | 310 |     |     |     |     | 315 |     |     |     |     |

It is proposed that the protein contains a 21 amino acid hydrophobic leader sequence which is cleaved to produce the following 298 amino acid mature protein with the known N-terminal sequence (amino acids 22–319 of SEQ ID NO:22).

domains), a highly hydrophobic transmembrane domain of 24–27 amino acids, and a highly polar intracellular C-terminal tail. This general structure is suggestive of the molecule being involved in signal transduction.

| Ile | Ser | Val | Glu | Thr 5 | Pro | Gln | Asp | Val | Leu 10 | Arg | Ala | Ser | Gln | Gly 15 | Lys |
| Ser | Val | Thr | Leu 20 | Pro | Cys | Thr | Tyr | His 25 | Thr | Ser | Thr | Ser | Ser 30 | Arg | Glu |
| Gly | Leu | Ile 35 | Gln | Trp | Asp | Lys | Leu 40 | Leu | Leu | Thr | His | Thr 45 | Glu | Arg | Val |
| Val | Ile 50 | Trp | Pro | Phe | Ser | Asn 55 | Lys | Asn | Tyr | Ile | His 60 | Gly | Glu | Leu | Tyr |
| Lys 65 | Asn | Arg | Val | Ser | Ile 70 | Ser | Asn | Asn | Ala | Glu 75 | Gln | Ser | Asp | Ala | Ser 80 |
| Ile | Thr | Ile | Asp | Gln 85 | Leu | Thr | Met | Ala | Asp 90 | Asn | Gly | Thr | Tyr | Glu 95 | Cys |
| Ser | Val | Ser | Leu 100 | Met | Ser | Asp | Leu | Glu 105 | Gly | Asn | Thr | Lys | Ser 110 | Arg | Val |
| Arg | Leu | Leu 115 | Val | Leu | Val | Pro | Pro 120 | Ser | Lys | Pro | Glu | Cys 125 | Gly | Ile | Glu |
| Gly | Glu 130 | Thr | Ile | Ile | Gly | Asn 135 | Asn | Ile | Gln | Leu | Thr 140 | Cys | Gln | Ser | Lys |
| Glu 145 | Gly | Ser | Pro | Thr | Pro 150 | Gln | Tyr | Ser | Trp | Lys 155 | Arg | Tyr | Asn | Ile | Leu 160 |
| Asn | Gln | Glu | Gln | Pro 165 | Leu | Ala | Gln | Pro | Ala 170 | Ser | Gly | Gln | Pro | Val 175 | Ser |
| Leu | Lys | Asn | Ile 180 | Ser | Thr | Asp | Thr | Ser 185 | Gly | Tyr | Tyr | Ile | Cys 190 | Thr | Ser |
| Ser | Asn | Glu 195 | Glu | Gly | Thr | Gln | Phe 200 | Cys | Asn | Ile | Thr | Val 205 | Ala | Val | Arg |
| Ser | Pro 210 | Ser | Met | Asn | Val | Ala 215 | Leu | Tyr | Val | Gly | Ile 220 | Ala | Val | Gly | Val |
| Val 225 | Ala | Ala | Leu | Ile | Ile 230 | Ile | Gly | Ile | Ile | Ile 235 | Tyr | Cys | Cys | Cys 240 |
| Arg | Gly | Lys | Asp | Asp 245 | Asn | Thr | Glu | Asp | Lys 250 | Glu | Asp | Ala | Arg | Pro 255 | Asn |
| Arg | Glu | Ala | Tyr 260 | Glu | Glu | Pro | Pro | Glu 265 | Gln | Leu | Arg | Glu | Leu 270 | Ser | Arg |
| Glu | Arg | Glu 275 | Glu | Glu | Asp | Asp | Tyr 280 | Arg | Gln | Glu | Glu | Gln 285 | Arg | Ser | Thr |
| Gly | Arg 290 | Glu | Ser | Pro | Asp | His 295 | Leu | Asp | Gln |

The position of the first in-frame stop codon predicts a polypeptide chain, which has a $M_r$ of 33276. Based on a hydrophilicity plot constructed from the amino acid sequence, the molecule appears to have three portions: an extracellular region of 213 amino acids (which by sequence alignment appears to contain two immunoglobulin-like The cDNA sequence starting at base pair 113 from the 5' end of clone 11, to base pair 1070 of clone 11, which encodes the 298 amino acid protein is as follows (SEQ ID NO: 23):

```
ATGGTGGGA  AGATGTGGCC  TGTGTTGTGG  ACACTCTGTG  CAGTCAGGGT  GACCGTCGAT
GCCATCTCTG  TGGAAACTCC  GCAGGACGTT  CTTCGGGCTT  CGCAGGGAAA  GAGTGTCACC
CTGCCCTGCA  CCTACCACAC  TTCCACCTCC  AGTCGAGAGG  GACTTATTCA  ATGGGATAAG
CTCCTCCTCA  CTCATACGGA  AAGGGTGGTC  ATCTGGCCGT  TTTCAAACAA  AAACTACATC
CATGGTGAGC  TTTATAAGAA  TCGCGTCAGC  ATATCCAACA  ATGCTGAGCA  GTCCGATGCC
TCCATCACCA  TTGATCAGCT  GACCATGGCT  GACAACGGCA  CCTACGAGTG  TTCTGTCTCG
CTGATGTCAG  ACCTGGAGGG  CAACACCAAG  TCACGTGTCC  GCCTGTTGGT  CCTCGTGCCA
CCCTCCAAAC  CAGAATGCGG  CATCGAGGGA  GAGACCATAA  TTGGGAACAA  CATCCAGCTG
ACCTGCCAAT  CAAAGGAGGG  CTCACCAACC  CCTCAGTACA  GCTGGAAGAG  GTACAACATC
CTGAATCAGG  AGCAGCCCCT  GGCCCAGCCA  GCCTCAGGTC  AGCCTGTCTC  CCTGAAGAAT
ATCTCCACAG  ACACATCGGG  TTACTACATC  TGTACCTCCA  GCAATGAGGA  GGGGACGCAG
TTCTGCAACA  TCACGGTGGC  CGTCAGATCT  CCCTCCATGA  ACGTGGCCCT  GTATGTGGGC
ATCGCGGTGG  GCGTGGTTGC  AGCCCTCATT  ATCATTGGCA  TCATCATCTA  CTGCTGCTGC
TGCCGAGGGA  AGGACGACAA  CACTGAAGAC  AAGGAGGATG  CAAGGCCGAA  CCGGGAAGCC
```

| | | | | | |
|---|---|---|---|---|---|
| TATGAGGAGC | CACCAGAGCA | GCTAAGAGAA | CTTTCCAGAG | AGAGGGAGGA | GGAGGATGAC |
| TACAGGCAAG | AAGAGCAGAG | GAGCACTGGG | CGTGAATCCC | CGGACCACCT | CGACCAGTGA |

Comparison with available DNA and protein databases revealed that the protein was novel. However, analysis of available expressed sequence tag (EST) databases revealed 74% sequence similarity between part of the human A33 antigen cDNA (nucleotides 286–529) and a 249 base pair EST derived from the murine embryonal carcinoma cell line F9 (EMBL Accession No. MM88A09; DDBJ Accession No. D28657). In the likelihood that this EST corresponded to part of the murine homologue of the human A33 antigen cDNA, sense and antisense PCR primers (17 mers) were designed to hybridize to the extremities of the EST clone, as follows:

Primer #1867 (F9 A33 sense) 5'TGACAAAGAAATACATC (SEQ ID NO: 24)
Primer #1868 (F9 A33 antisense) 5'TCTGGCTTG-GAGGGTGG (SEQ ID NO: 25)

These primers were used in the touchdown PCR program described above to amplify a 218 bp product from a normal adult mouse colonic crypt cDNA library (J. Biol. Chem. Vol. 268, pp. 27214–27225 (1993)). This product was gel-purified and DNA sequencing demonstrated that this product closely corresponded to the F9 EST:

contains errors and that the authentic sequence is better described by the sequence of the PCR product described herein.

The A33 antigen which has now been isolated, characterized and sequenced, can be used to diagnose colon cancer which is characterized by the presence of the A33 antigen. For example, a sample suspected of containing colon cancer cells is contacted with an antibody specific for the A33 antigen or a fragment thereof, so that A33 protein/antibody complexes can be formed. If these complexes are present, a positive colon cancer diagnosis is indicated.

In addition, the A33 antigen can be used to identify ligands which bind to it (binding partners). The A33 antigen can be isolated, or recombinantly expressed, and used to screen biological sources, including tissue culture media, tissue extracts and cell lysates, for binding partners. Once a binding partner has been found, it is isolated and purified, and can be sequenced. This can be done with the use of a biosensor, in combination with affinity and other chromatographic techniques. Optionally, the A33 antigen can be tagged, to assist in immobilization of the antigen in a specific orientation onto the biosensor surface or affinity support. Identifying binding partners can be done utilizing techniques known to those skilled in the art. See, for Seq 1 (SEQ ID NO: 26)
MM88A09 EST sequence (nucleic)
Seq 2 (SEQ ID NO: 27)
mouse colon cDNA (PCR product)

Seq 1
5' AGTATCTAACGAGTGCTGAGGTTGTCAAATGCCTCTATCACCATCGACCAGCTGACCATGGA
Seq 2
5' AGTATCTAACGA-TGCTGAG-TTGTCAAATGCCTCTATCACCATCGACCAGCTGACCATGGA
Seq 1
CGACAATGGCACCTACGAGTGCTCCGGTGTCACTGATGTCGGACCAGGATGTCAACGCCAA
Seq 2
CGACAATGGCACCTACGAGTGCTCCG-TGTCACTGATGTCGGACCAGGATGTCAACGCCAA

Translation of the murine colonic PCR product revealed significant homology with part of the sequence of the A33 antigen (residues 64–104). The alignment between the predicted human and murine protein sequences is shown below:

example, Stitt et al., Cell, Vol. 80, pp. 661–670 (1995), Nice et al., J. Chromatography A., Vol. 660, pp. 169–185 (1994) and Bartley et al., Nature, Vol. 368, p. 558 (1994).

Human (amino acids 85–125 of SEQ ID NO: 22)
Y K N R V S I S N N A E Q S D A S I T I D Q T M A D N G T Y E C
S V S L M S D L
104
Murine (SEQ ID NO: 29)
Y E N R V R V S N D A E L S N A S I T I D O L T M D D N G T Y E C
S V S L M S D Q The F9 PCR product was radiolabelled and used as a probe in Northern analysis of multiple murine tissue RNAs (from colonic crypts, small intestinal crypts, kidney, liver, brain, spleen, thymus, lung). An intense band of approximately 2.6 kb in size was seen only in the lanes containing RNA prepared from colonic crypts and small intestinal crypts. This close correspondence with the size of human A33 antigen mRNA, together with the alignment shown above and the restricted tissue expression, strongly suggests that the F9 clone encodes the murine homologue of the A33 antigen. In addition, these data suggest that the F9 EST Further, the cDNA encoding A33 antigen has been described herein. This cDNA, including the untranslated portions at the 5' and 3' ends, easily facilitates the production of A33 antigen double-stranded cDNA molecules from tissues and cell lines expressing the A33 antigen, and A33 antigen genomic clones from Senomic DNA. To do this, the A33 cDNA is used to design complementary primers for use in the technique of RT-PCR (reverse transcriptase-PCR), a standard procedure for the production of double-stranded cDNA molecules from mRNA templates. Further, the A33 cDNA can be used to design complementary primers for use in standard PCR reactions to amplify portions of the A33 antigen gene from genomic DNA templates.

It is possible that the A33 antigen resides in a novel family of related signal transduction molecules proteins. The A33 cDNA sequence described herein can be used to design specific and degenerate oligonucleotide primers for use in low stringency PCR reactions to amplify portions of cDNA and genomic DNA molecules encoding proteins related to the A33 antigen. In addition, the A33 cDNA can be used to design specific and degenerate oligonucleotide probes for the identification of members of the A33 antigen gene family by Southern analysis of genomic DNA under low stringency conditions.

These procedures utilizing A33 cDNA are standard procedures, known to those skilled in the art of molecular biology. See, for example, Molecular Cloning: A Laboratory Manual, 2nd edition, 1989 (eds. Sambrook J., Fritsch E. F. & Maniatis T.) Cold Spring Harbor Laboratory Press, U.S.A., and Current Protocols in Molecular Biology Volumes I & II, 1989 (ed. Ausubel, F. M.) Greene Publishing Associates and Wiley-Interscience, U.S.A.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. Isolated protein containing molecule the protein portion of which has a molecular weight of about 43 kD as determined by SDS-PAGE under non-reducing conditions, wherein said molecule binds to monoclonal antibody A33.

2. The isolated protein containing molecule of claim 1, wherein said molecule is recombinant.

3. Isolated protein containing molecule consisting of the amino acid sequence set forth by SEQ ID NO: 22 or amino acids 22–319 of SEQ ID NO:22.

4. The isolated protein containing molecule of claim 3, wherein cys43 and cys117 are linked by a disulfide bond.

5. Isolated peptide molecule which consists of an antigenic fragment of the amino acid sequence of SEQ ID NO: 22, wherein said peptide binds to monoclonal antibody A33.

6. The isolated peptide of claim 5, wherein said peptide consists of an amino acid sequence selected from the group consisting of SEQ. ID. NOS. 1, 2, 3, 4, 5, 6, 7, 8, 9, 10 and 11.

7. The isolated peptide of claim 5, wherein said peptide is recombinant.

* * * * *